US012600954B2

(12) United States Patent
Du et al.

(10) Patent No.: US 12,600,954 B2
(45) Date of Patent: Apr. 14, 2026

(54) METHOD FOR PREPARING HEMOGENIC ENDOTHELIUM CELL AND METHOD FOR PREPARING HEMATOPOIETIC STEM CELL OR HEMATOPOIETIC STEM AND PROGENITOR CELL

(71) Applicant: ALLIFE MEDICINE (BEIJING) LIMITED, Beijing (CN)

(72) Inventors: Rulong Du, Beijing (CN); Lei Yu, Beijing (CN); Wenjing Huang, Beijing (CN); Xuening Wu, Beijing (CN); Yuchun Gu, Beijing (CN); Lida Wu, Beijing (CN)

(73) Assignee: ALLIFE MEDICINE (BEIJING) LIMITED, Beijing (CN)

( * ) Notice: Subject to any disclaimer, the term of this patent is extended or adjusted under 35 U.S.C. 154(b) by 0 days.

(21) Appl. No.: 19/083,713

(22) Filed: Mar. 19, 2025

(65) Prior Publication Data

US 2025/0250544 A1 Aug. 7, 2025

Related U.S. Application Data

(63) Continuation of application No. PCT/CN2023/074734, filed on Feb. 7, 2023.

(30) Foreign Application Priority Data

Sep. 21, 2022 (CN) .......................... 202211147815.3

(51) Int. Cl.
| | |
|---|---|
| *C12N 5/071* | (2010.01) |
| *C07K 14/47* | (2006.01) |
| *C12N 5/00* | (2006.01) |
| *C12N 15/86* | (2006.01) |

(52) U.S. Cl.
CPC ........ *C12N 5/0692* (2013.01); *C07K 14/4702* (2013.01); *C12N 5/0018* (2013.01); *C12N 15/86* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2303* (2013.01); *C12N 2501/26* (2013.01); *C12N 2501/999* (2013.01); *C12N 2506/45* (2013.01); *C12N 2750/14143* (2013.01)

(58) Field of Classification Search
CPC .... C12N 5/0692; C12N 5/0018; C12N 15/86; C07K 14/4702
See application file for complete search history.

(56) References Cited

U.S. PATENT DOCUMENTS

| | | | |
|---|---|---|---|
| 2010/0317104 A1* | 12/2010 | Elefanty et al. | |
| 2019/0119643 A1 | 4/2019 | Daley et al. | |
| 2020/0199535 A1 | 6/2020 | Daley | |
| 2021/0355441 A1 | 11/2021 | Slukvin et al. | |
| 2024/0191205 A1 | 6/2024 | Wu et al. | |

FOREIGN PATENT DOCUMENTS

| | | |
|---|---|---|
| CN | 103937743 A | 7/2014 |
| CN | 106867961 A | 6/2017 |
| CN | 108220243 A | 6/2018 |
| CN | 109913494 A | 6/2019 |
| CN | 110577967 A | 12/2019 |
| CN | 111321110 A | 6/2020 |
| CN | 111440760 A | 7/2020 |
| CN | 111607566 A | 9/2020 |
| CN | 114181968 A | 3/2022 |
| CN | 114269906 A | 4/2022 |
| CN | 115029314 A | 9/2022 |
| CN | 115247151 A | 10/2022 |
| WO | 2020154412 A1 | 7/2020 |
| WO | 2020243613 A1 | 12/2020 |
| WO | 2021262698 A2 | 12/2021 |

OTHER PUBLICATIONS

Dzierzak E, Bigas A. Blood Development: Hematopoietic Stem Cell Dependence and Independence. Cell Stem Cell. 2018;22(5):639-651. doi:10.1016/j.stem.2018.04.015 (Year: 2018).*

Gritz E, Hirschi KK. Specification and function of hemogenic endothelium during embryogenesis. Cell Mol Life Sci. 2016;73(8):1547-1567. doi: 10.1007/s00018-016-2134-0 (Year: 2016).*

Luff SA, Fernandez NA, Sturgeon CM, Ditadi A. Generation of functionally distinct hemogenic endothelial cell populations from pluripotent stem cells. Exp Hematol. 2024;138:104587. doi:10.1016/j.exphem.2024.104587 (Year: 2024).*

International Search Report in PCT/CN2023/074734 mailed on Jun. 21, 2023, 6 pages.

Written Opinion in PCT/CN2023/074734 mailed on Jun. 21, 2023, 5 pages.

Abuhantash, M. et al., Role of the HOXA Cluster in HSC Emergence and Blood Cancer, Biochemical Society Transactions, 49: 1817-1827, 2021.

Shim, S. H. et al., SAHA Enhances Differentiation of CD34+CD45+ Hematopoietic Stem and Progenitor Cells from Pluripotent Stem Cells Concomitant with an Increase in Hemogenic Endothelium, Stem Cells Translational Medicine, 11(2): 513-526, 2022.

(Continued)

*Primary Examiner* — Teresa E Knight
*Assistant Examiner* — Kodye Lee Abbott
(74) *Attorney, Agent, or Firm* — PORUS IP LLC

(57) ABSTRACT

A method for preparing hematopoietic endothelial cells and a method for preparing hematopoietic stem cells are provided, comprising inducing hematopoietic mesodermal cells to express transcription factors LCOR, HOXA9, HOXA5, RUNX1, and ERG at specific time periods during the conversion of induced pluripotent stem cells into the hematopoietic endothelial cells or the hematopoietic stem cells. The method can increase the preparation efficiency of at least one of the hematopoietic endothelial cells and the hematopoietic stem cells (including long-term hematopoietic stem cells).

11 Claims, 28 Drawing Sheets

(56)             References Cited

OTHER PUBLICATIONS

Hou, S. et al., Embryonic Endothelial Evolution Towards First Hematopoietic Stem Cells Revealed by Single-Cell Transcriptomic and Functional Analyses, Cell Research, 30: 376-392, 2020.

Tomellini, E. et al., Integrin-A3 is a Functional Marker of Ex Vivo Expanded Human Long-Term Hematopoietic Stem Cells, Cell Reports, 2019, 17 pages.

Giebel, B. et al., Self-Renewal Versus Differentiation in Hematopoietic Stem and Progenitor Cells: A Focus on Asymmetric Cell Divisions, Current Stem Cell Research & Therapy, 3(1): 9-16, 2008.

Seita, J. et al., Hematopoietic Stem Cell: Self-renewal Versus Differentiation, Wiley Interdisciplinary Reviews Systems Biology and Medicine, 2010, 20 pages.

Lis, R. et al., Conversion of Adult Endothelium to Immunocompetent Haematopoietic Stem Cells, Nature, 2017, 43 pages.

Sandler, V. M. et al., Reprogramming Human Endothelial to Hematopoietic Cells Requires Vascular Induction, Nature, 2014, 43 pages.

First Office Action in Chinese Application No. 202211147815.3 mailed on Nov. 4, 2022, 29 pages.

Notification to Grant Patent Right for Invention in Chinese Application No. 202211147815.3 mailed on Nov. 24, 2022, 6 pages.

Zhang, Qingyun et al., Research Advance on In Vitro Generation of Human Hematopoietic Stem Cells for Transplantation, Journal of Experimental Hematology, 28(1): 320-324, 2020.

Ryohichi Sugimura et al., Haematopoietic stem and progenitor cells from human pluripotent stem cells, Nature, 545(7655): 432-438, 2017.

* cited by examiner

B

C

D

D

E

METHOD FOR PREPARING HEMOGENIC ENDOTHELIUM CELL AND METHOD FOR PREPARING HEMATOPOIETIC STEM CELL OR HEMATOPOIETIC STEM AND PROGENITOR CELL

CROSS-REFERENCE TO RELATED APPLICATIONS

The present application is a Continuation of International Application No. PCT/CN2023/074734, filed on Feb. 7, 2023, which claims priority to Chinese Patent Application No. 202211147815.3, filed on Sep. 21, 2022, the entire contents of each of which are incorporated herein by reference.

TECHNICAL FIELD

The present disclosure relates to the field of cellular technology, and in particular, to methods for preparing hematopoietic endothelial cells and methods for preparing hematopoietic stem cells or hematopoietic stem and progenitor cells.

BACKGROUND

Hematopoietic Stem Cells (HSCs) are adult stem cells with self-renewal and differentiation potential, which are capable of differentiating into all blood cells and platelets. The HSCs can be used for the treatment of related blood diseases such as leukemia and lymphoma by cell transplantation. Meanwhile, the HSCs can also be differentiated into various blood cells and the platelets in vitro for clinical treatment and research. At present, the HSCs are mainly isolated from the body. However, due to the shortcomings such as low content of the HSCs and the inability to culture the HSCs for a long period of time in vitro, the clinical research and application of the HSCs are seriously restricted. Pluripotent Stem Cells (PSCs) are cells with self-renewal and differentiation potential, including Embryonic Stem Cells (ESCs), induced Pluripotent Stem Cells (iPSCs), Extended Pluripotent Stem Cells (EPSCs), Totipotent Stem Cells (TPSCs), etc. The PSCS can be induced to differentiate into the HSCs, which provides a new option and pathway for transplantation and clinical application of the HSCs. However, the current induced differentiation methods can only obtain Hematopoietic Progenitor Cells (HP Cs) with limited differentiation potential and no long-term self-renew capacity, but not obtain long-term HSCs. The current differentiation methods have numerous defects, including low induction efficiency, long differentiation cycle, complicated differentiation process, differentiation medium containing animal-derived components, etc. These defects seriously limit the clinical research and application of the HSCs.

SUMMARY

One or more embodiments of the present disclosure provide a method for preparing hematopoietic endothelial cells, comprising:
    (a) providing hematopoietic mesodermal cells or a cell culture comprising the hematopoietic mesodermal cells;
    (b) culturing the hematopoietic mesodermal cells or the cell culture comprising the hematopoietic mesodermal cells in a hematopoietic endothelial differentiation medium; and (c) inducing the hematopoietic mesodermal cells to express transcription factors LCOR, HOXA9, HOXA5, RUNX1, and ERG.

In some embodiments, in step (c), the hematopoietic mesodermal cells overexpress the transcription factors LCOR, HOXA9, HOXA5, RUNX1, and ERG.

In some embodiments, the step (c) is performed for 4 days.

In some embodiments, the step (c) is performed on days 1-4 or days 4-7 of the culturing in step (b).

In some embodiments, the hematopoietic endothelial differentiation medium comprises VEGF, bFGF, SCF, IL-3, TPO, Flt-3L, and BMP4.

In some embodiments, the hematopoietic endothelial differentiation medium is a STEMdiff™ APEL™2 medium supplemented with VEGF, bFGF, SCF, IL-3, TPO, Flt-3L, and BMP4.

In some embodiments, the hematopoietic mesodermal cells comprise exogenously introduced nucleic acid sequences encoding the transcription factors LCOR, HOXA9, HOXA5, RUNX1, and ERG.

In some embodiments, the nucleic acid sequences encoding the transcription factors LCOR, HOXA9, HOXA5, RUNX1, and ERG are operably linked to an inducible promoter.

In some embodiments, the inducible promoter is a tetracycline-inducible promoter. In some embodiments, the hematopoietic mesodermal cells further comprise an exogenously introduced nucleic acid sequence encoding rtTA.

In some embodiments, the nucleic acid sequences encoding the transcription factors LCOR, HOXA9, HOXA5, RUNX1, and ERG, and the nucleic acid sequence encoding rtTA are integrated in a genome of the hematopoietic mesodermal cells.

In some embodiments, in the step (c), the hematopoietic mesodermal cells are induced to express the transcription factors LCOR, HOXA9, HOXA5, RUNX1, and ERG by adding tetracycline or doxycycline to the hematopoietic endothelial differentiation medium.

In some embodiments, the hematopoietic mesodermal cells or the cell culture comprising the hematopoietic mesodermal cells are obtained by culturing mesodermal cells or a cell culture comprising the mesodermal cells in a hematopoietic mesoderm differentiation medium.

In some embodiments, the hematopoietic mesodermal cells or the cell culture comprising the hematopoietic mesodermal cells are obtained by culturing the mesodermal cells or the cell culture comprising the mesodermal cells in the hematopoietic mesoderm differentiation medium for 2 days.

In some embodiments, the hematopoietic mesoderm differentiation medium comprises VEGF and bFGF.

In some embodiments, the hematopoietic mesoderm differentiation medium is a STEMdiff™ APEL™ 2 medium supplemented with VEGF and bFGF.

In some embodiments, the mesodermal cells or the cell culture comprising the mesodermal cells are obtained by performing a mesoderm induction on pluripotent stem cells (PSCs), the pluripotent stem cells are induced pluripotent stem cells (iPSCs), and the induced pluripotent stem cells are human induced pluripotent stem cells.

In some embodiments, the pluripotent stem cells comprise the exogenously introduced nucleic acid sequences encoding the transcription factors of LCOR, HOXA9, HOXA5, RUNX1, and ERG. In some embodiments, the introduction is carried out by a lentiviral vector.

In some embodiments, the hematopoietic endothelial cells are CD34⁺, KDR⁺, and CD144⁺.

In some embodiments, the hematopoietic mesodermal cells are KDR$^+$ and PDGFR$\alpha^-$.

In some embodiments, the mesodermal cells are Braychury$^+$.

One or more embodiments of the present disclosure provide a method for preparing hematopoietic stem cells or hematopoietic stem and progenitor cells, comprising:

(1) providing hematopoietic mesodermal cells or a cell culture comprising the hematopoietic mesodermal cells;

(2) culturing the hematopoietic mesodermal cells or the cell culture comprising the hematopoietic mesodermal cells in a hematopoietic endothelial differentiation and endothelial-to-hematopoietic transition medium; and (3) inducing the hematopoietic mesodermal cells to express the transcription factors LCOR, HOXA9, HOXA5, RUNX1, and ERG;

In some embodiments, in step (3), the hematopoietic mesodermal cells overexpress the transcription factors LCOR, HOXA9, HOXA5, RUNX1, and ERG.

In some embodiments, the step (3) is performed on 3 days after step (2).

In some embodiments, the step (3) is performed for at least 7 days.

In some embodiments, the step (3) is performed on days 4-10 of the culturing in the step (2).

In some embodiments, the hematopoietic endothelial differentiation and endothelial-to-hematopoietic transition medium comprises VEGF, bFGF, SCF, IL-3, TPO, Flt-3L, and BMP4.

In some embodiments, the hematopoietic endothelial differentiation and endothelial-to-hematopoietic transition medium is a STEMdiff™ APEL™ 2 medium supplemented with VEGF, bFGF, SCF, IL-3, TPO, Flt-3L, and BMP4.

In some embodiments, the hematopoietic mesodermal cells comprise the exogenously introduced nucleic acid sequences encoding the transcription factors LCOR, HOXA9, HOXA5, RUNX1, and ERG.

In some embodiments, the nucleic acid sequences encoding the transcription factors LCOR, HOXA9, HOXA5, RUNX1, and ERG are operably linked to the inducible promoter.

In some embodiments, the inducible promoter is the tetracycline-inducible promoter. In some embodiments, the hematopoietic mesodermal cells further comprise the exogenously introduced nucleic acid sequence encoding rtTA.

In some embodiments, the nucleic acid sequences encoding the transcription factors LCOR, HOXA9, HOXA5, RUNX1, and ERG, and the nucleic acid sequence encoding rtTA are integrated in a genome of the hematopoietic mesodermal cells.

In some embodiments, in the step (3), the hematopoietic mesodermal cells are induced to express the transcription factors LCOR, HOXA9, HOXA5, RUNX1, and ERG by adding the tetracycline or the doxycycline to the hematopoietic endothelial differentiation and endothelial-to-hematopoietic transition medium.

In some embodiments, the hematopoietic mesodermal cells or the cell culture comprising the hematopoietic mesodermal cells are obtained by culturing the mesodermal cells or the cell culture comprising the mesodermal cells in a hematopoietic mesoderm differentiation medium.

In some embodiments, the hematopoietic mesodermal cells or the cell culture comprising the hematopoietic mesodermal cells are obtained by culturing the mesodermal cells or the cell culture comprising the mesodermal cells in the hematopoietic mesoderm differentiation medium for 2 days.

In some embodiments, the hematopoietic mesoderm differentiation medium comprises VEGF and bFGF.

In some embodiments, the hematopoietic mesoderm differentiation medium is a STEMdiff™ APEL™ 2 medium supplemented with VEGF and bFGF.

In some embodiments, the mesodermal cells or the cell culture comprising the mesodermal cells are obtained by performing the mesoderm induction on the pluripotent stem cells.

In some embodiments, the pluripotent stem cells comprise the exogenously introduced nucleic acid sequences encoding the transcription factors LCOR, HOXA9, HOXA5, RUNX1, and ERG. In some embodiments, the introduction is carried out by the lentiviral vector.

In some embodiments, the hematopoietic mesodermal cells are KDR$^+$ and PDGFR$\alpha^-$.

In some embodiments, the hematopoietic stem cells are CD34$^+$CD45RA$^-$CD90$^+$EPCR$^+$.

In some embodiments, the hematopoietic stem cells are long-term hematopoietic stem cells.

In some embodiments, the long-term hematopoietic stem cells are CD34$^+$EPCR$^+$CD90$^+$ITGA3$^+$. In some embodiments, the hematopoietic stem and progenitor cells are CD34$^+$ and CD45$^+$.

BRIEF DESCRIPTION OF THE DRAWINGS

The present disclosure will be further illustrated by way of exemplary embodiments, which are described in detail by means of the accompanying drawings. These embodiments are not limiting, wherein:

FIG. 2A is fluorescence images of EGFP expression induced by DOX added in 293T cells transfected with pLenti-EF1$\alpha$-rtTA-IRES-PuroR and TetO-FUW-EGFP-EF1$\alpha$-NeoR plasmids, Control represents addition of no doxycycline, and DOX represents addition of 5 µg/mL doxycycline; FIG. 2B is flow cytometry analysis of EGFP$^+$ cell efficiency in 293T cells transfected with the pLenti-EF1$\alpha$-rtTA-IRES-PuroR and the TetO-FUW-EGFP-EF1$\alpha$-NeoR plasmids followed by addition of DOX, Control represents addition of no doxycycline, and DOX represents addition of 5 µg/mL doxycycline; FIG. 2C is fluorescence images of EGFP expression induced by DOX added in hiPS-001-5 cells transfected with the pLenti-EF1$\alpha$-rtTA-IRES-PuroR and the TetO-FUW-EGFP-EF1$\alpha$-NeoR plasmids, Control represents addition of no doxycycline, and DOX represents addition of 5 µg/mL doxycycline; FIG. 2D is flow cytometry analysis of EGFP$^+$ cell efficiency in hiPS-001-5 cells transfected with the pLenti-EF1$\alpha$-rtTA-IRES-PuroR and the TetO-FUW-EGFP-EF1$\alpha$-NeoR plasmids followed by the addition of DOX, Control represents addition of no doxycycline, and the DOX represents addition of 5 µg/mL doxycycline; FIG. 2E is brightfield images of the cytotoxicity test of different concentrations of G418 (100-600 µg/mL) on hiPS-001-5 cells, and Control represents addition of no G428; FIG. 2F is brightfield images of the cytotoxicity test of different concentrations of Blasticidin (2.5-40 µg/mL) on the hipS-001-5 cells, and Control represents addition of no Blasticidin; FIG. 2G is brightfield images of the cytotoxicity test of different concentrations of Puromycin (0.25-4 µg/mL) on the hiPS-001-5 cells, and Control represents addition of no Puromycin;

FIG. 3A is charts illustrating the induced expression of LCOR, HOXA9, HOAX5, RUNX1, and ERG genes at the transcription level in the hiPS 001-5-LHHRE cell line after 3 days of DOX treatment by a qRT-PCR analysis, "–" represents the addition of no DOX, and "+" represents the addition of DOX (5 µg/mL doxycycline); FIG. 3B is flow cytometry analysis of differentiation efficiency of CD34$^+$KDR$^+$CD144$^+$hematopoietic endothelial cells induced by the addition of 5 µg/mL doxycycline on D3-6 and D6-9 during the differentiation on day 9, Control represents the addition of no DOX, D3-6 represents the addition of 5 µg/mL doxycycline on days 3-6 of the differentiation, and D6-9 represents the addition of 5 µg/mL doxycycline on days 6-9 of the differentiation; FIG. 3C is flow cytometry analysis of the differentiation efficiency of CD34$^+$CD45$^+$ hematopoietic cells induced by the addition of 5 µg/mL doxycycline at different time windows during the differentiation on day 12, Control represents the addition of no DOX, D3-12 represents the addition of 5 µg/mL doxycycline on days 3-12 of the differentiation, D6-12 represents the addition of 5 µg/mL doxycycline on days 6-12 of the differentiation, D9-12 represents the addition of 5 µg/mL doxycycline on days 9-12 of the differentiation; FIG. 3D is flow cytometry analysis of the differentiation efficiency of CD34$^+$CD90$^+$EPCR$^+$ITGA3$^+$ long term repopulating hematopoietic stem cells induced by the addition of 5 µg/mL doxycycline during the differentiation on day 12, Control represents the addition of no doxycycline, and DOX represents the addition of 5 µg/mL doxycycline on days 6-12 of the differentiation; FIG. 3E is flow cytometry analysis of the differentiation efficiency of CD34$^+$CD45RA$^-$CD90$^+$EPCR$^+$ hematopoietic stem cells induced by the addition of 5 µg/mL doxycycline during the differentiation on day 12, Control represents the addition of no doxycycline, and DOX represents the addition of 5 µg/mL doxycycline on days 6-12 of the differentiation;

FIG. 17A is bright-field images of colony units of erythrocyte (BFU-E and CFU-E), granulocyte (CFU-G), macrophage (CFU-M), granulocyte/macrophage (CFU-GM), and multilineage progenitor cell (CFU-GEMM) formed by culturing the hematopoietic stem cells obtained from induced differentiation in methyl cellulose medium for 14 days; FIG. 17B is a quantitative statistic chart of different types of colony units formed by culturing the hematopoietic stem cells obtained by induced differentiation in the methyl cellulose medium for 14 days; 001-5 represents the hematopoietic stem cells obtained by the differentiation of hipS-001-5; and LHHRE represents the hematopoietic stem cells obtained after induction of the hiPS-001-5-LHHRE by DOX.

DETAILED DESCRIPTION

Figure 1:
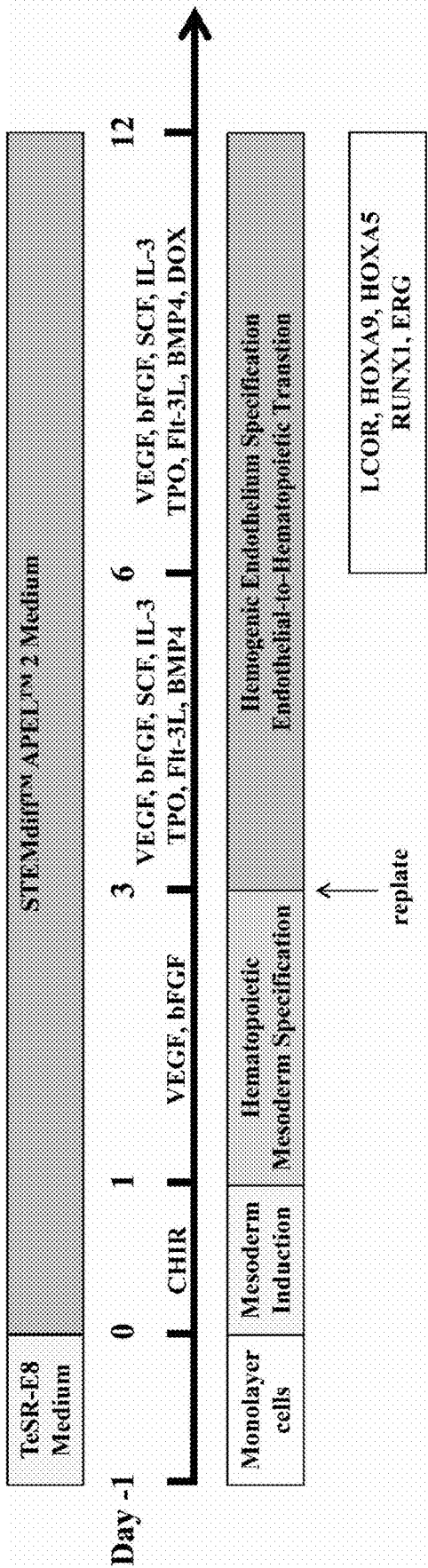
FIG. 1 is a flowchart of differentiation of human pluripotent stem cells (hiPS-001-5-LHHRE) to long-term repopulating hematopoietic stem cells according to some embodiments of the present disclosure.

All technical and scientific terms used in the present disclosure have the meanings commonly understood by a person of ordinary skill in the art, unless otherwise indicated.

The term "or" refers to a single element of an enumerated optional element, unless the context clearly indicates otherwise.

The term "at least one of" refers to any one, any two, any three, any more, or all of the enumerated optional elements.

The term "include" or "comprise" refers to including the elements, integers, or steps, but does not exclude any other elements, integers, or steps. Unless otherwise specified, the use of "include" or "comprise" also covers situations consisting of the elements, integers, or steps.

"Stem cells" refer to an undifferentiated or insufficiently differentiated cells, on the one hand, the stem cells are capable of self-renewing, i.e., producing more identical cells, and on the other hand, the stem cells are capable of differentiating into two or more mature cells. According to the source of the stem cells, the stem cells are able to be categorized into embryonic stem cells (ESCs) and adult stem cells. The ESCs may be derived from early animal embryos, e.g., an inner cell mass of a blastocyst (i.e., early embryo), and the ESCs has totipotency (the ability to differentiate into every type of cell in the body). The adult stem cells are found in various organs and tissues of the adult body and has pluripotency (the ability to differentiate and replace cells in the tissues in which the adult stem cells are located). Hematopoietic stem cells (HSCs) are the adult stem cells that are found in the bone marrow and has the ability to differentiate into various blood cells. The HSCs are capable of producing both myeloid and lymphoid progenitor cells, which further differentiate into myeloid cells (e.g., monocytes, macrophages, neutrophils, basophils, dendritic cells, erythrocytes, platelets, etc.) and lymphoid cells (e.g., T cells, B cells, NK cells, etc.). The ability of the stem cells to self-replicate and differentiate into a plurality or specific types of cells makes the stem cells central to cellular replacement therapies.

"Induced pluripotent stem cells (iPSCs)" refer to stem cells with totipotency or pluripotency obtained from certain adult cells (e.g., fibroblasts) by artificially inducing the expression of certain genes. In some manners known in the art, the iPSCs may be obtained by transfecting certain stem cells-related genes into non-pluripotent cells such as adult fibroblasts. The transfection may be achieved by viral transduction using viruses such as retroviruses or lentiviruses. In some embodiments, transfected genes may include transcription factors Oct4, Sox2, Klf4, and c-Myc, and transfection with other genes may improve the induction efficiency. In some embodiments, somatic cells are transformed by the transcription factors Oct4, Sox2, Nanog, and Lin28 by a lentiviral system. Genes induced to be expressed in the iPSCs include, but are not limited to, Oct-3/4, certain members of the Sox gene family (e.g., SoxI, Sox2, Sox3, and Sox15), certain members of the Klf family (e.g., KlfI, Klf2, Klf4, and Klf5), certain members of the Myc family (e.g., C-myc, L-myc, and N-myc), Nanog, Lin28, Tert, Fbx15, ERas, ECAT15-1, ECAT15-2, Tcl1, β-Catenin, ECAT1, Esg1, Dnmt3L, ECAT8, Gdf3, Fth117, Sal14, Rex1, UTF1, Stella, Stat3, Grb2, Prdm14, Nr5a1, Nr5a2, or E-cadherin, or any combination thereof. Various reagents for the preparation of the iPSCs may be purchased from the market, such as reprogramming vectors, expression cassettes, mediums, and even commercialized iPSCs. The hiPSC refers to iPSC induced from human cells. In some embodiments, the used hiPSC is prepared according to a manner (e.g., using the reprogramming factor combination OCT4, SOX2, E6, and E7) described in the Chinese patent disclosure CN113462638A, which is hereby incorporated herein by reference in its entirety.

Figure 6:
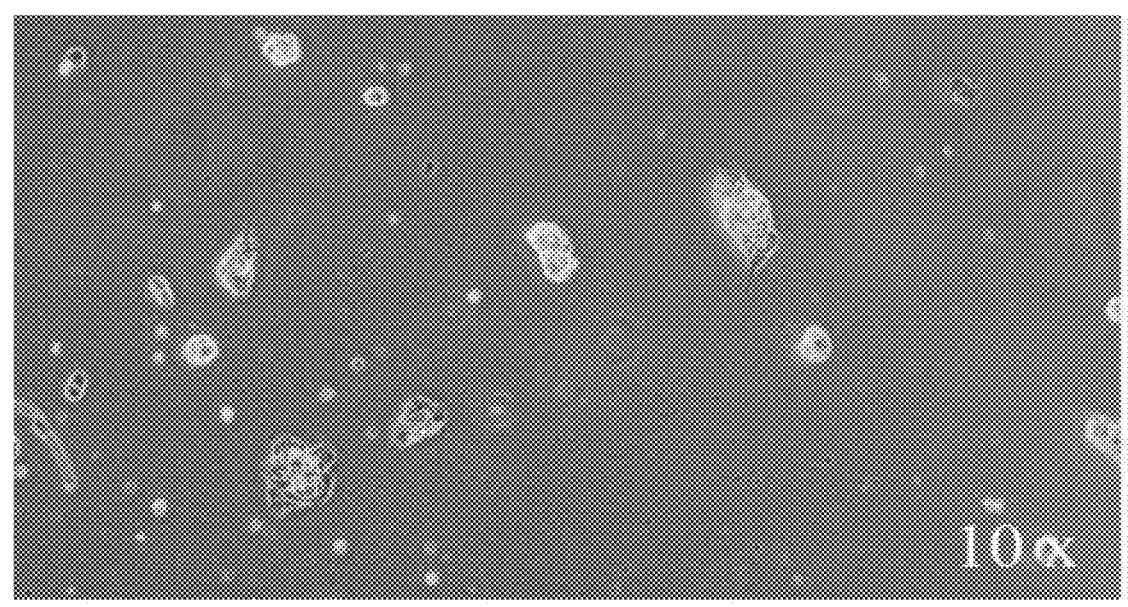
FIG. 6 is cell morphology images of the human pluripotent stem cells (hiPS-001-5-LHHRE) induced to differentiate into mesodermal cells (Day1) at the different magnifications according to some embodiments of the present disclosure.
Figure 6:
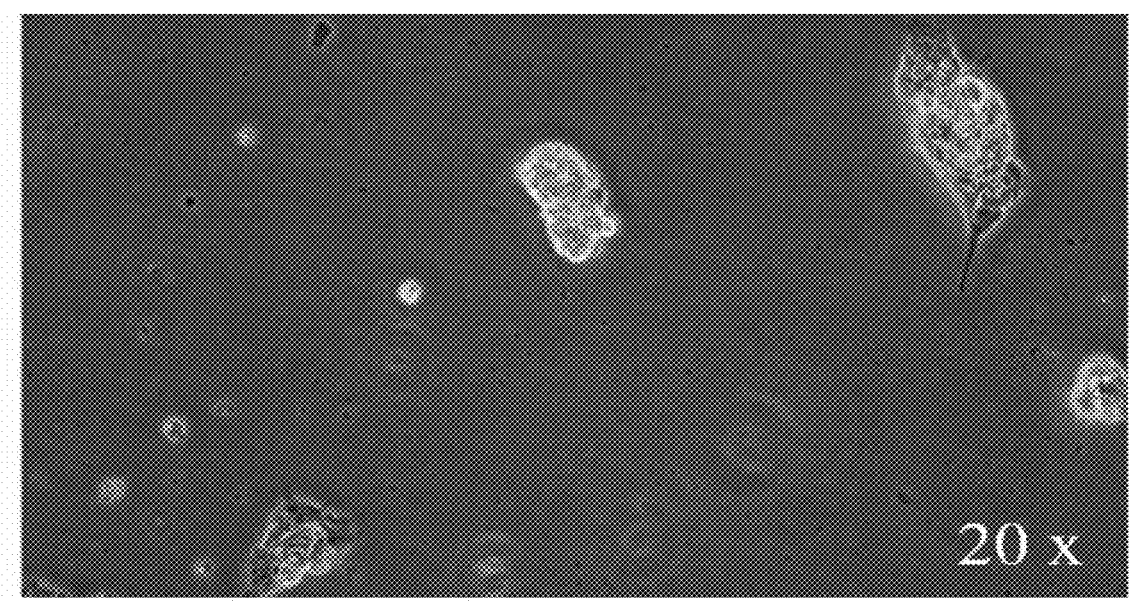

"Mesodermal cells" refer to a cell layer between the ectoderm and the endoderm at the late gastrula stage during embryonic development of a tri-embryonic animal. The mesodermal cells develop into the dermis, muscles, bones, and other connective tissues and circulatory system of the body, including the heart, blood vessels, bone marrow, lymph nodes, lymphatic vessels, the serous membranes and mesenteries of the end of the body cavity and the viscera, and connective tissues, blood vessels, and smooth muscles in viscera, kidneys, ureters, gonads (excluding germ cells), genital ducts, and the adrenal cortex. As used herein, the mesodermal cells refer to cells having mesodermal cells markers (e.g., Braychury) produced by culturing the iPSCs in a mesoderm induction medium. Accordingly, a process of inducing and culturing the iPSCs into the mesoderm cells is called "mesoderm induction". Methods for generating the mesodermal cells from the induced pluripotent stem cells (IPSCs) are known in the art, for example, the mesoderm induction medium is already commercially available, such as a STEMdiff™ mesoderm induction medium. Furthermore, Chinese patent disclosure CN 111321110 A describes a method for generating the mesodermal cells by inducing the iPSCs, and Chinese patent disclosure CN 106867961A describes a culture medium and method for generating the mesodermal cells from the iPSC induction, which are hereby incorporated herein by reference. In some embodiments, the mesodermal cells are obtained by culturing monolayer-adherent iPSCs in the mesoderm induction medium for 1 day (about 24 h). In some embodiments, the mesoderm induction phase may be extended, e.g., 1.5 days, 2 days, 3 days, etc., as long as the desired mesodermal cells are obtained. The present disclosure also provides cell morphology images of the hematopoietic mesodermal cells, as shown in FIG. 6.

Figure 8:
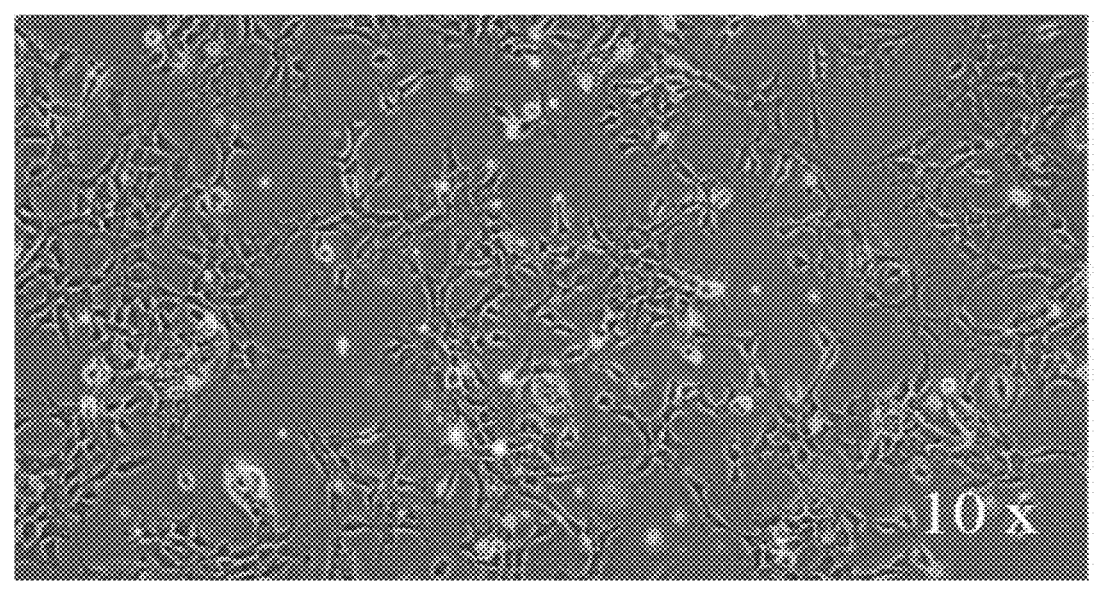
FIG. 8 is cell morphology images of the human pluripotent stem cells (hiPS-001-5-LHHRE) induced to differentiate into the hematopoietic mesodermal cells (Day3) at the different magnifications according to some embodiments of the present disclosure.
Figure 8:
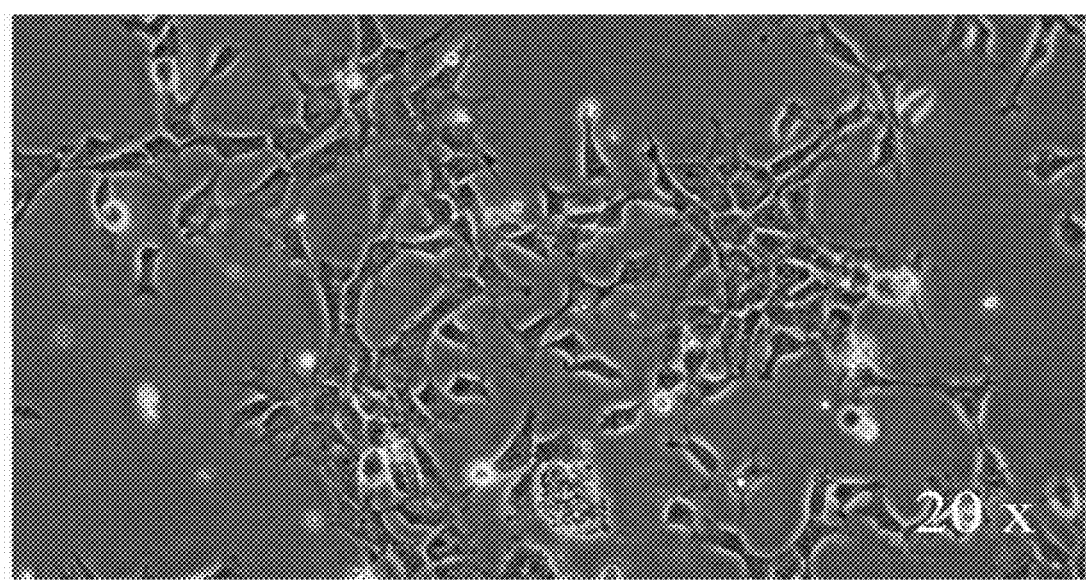

"Hematopoietic mesodermal differentiation" in the present disclosure refers to a process of inducing and differentiating the mesodermal cells into the "hematopoietic mesodermal cells". "Hematopoietic mesodermal cells" may be considered as precursor cells of the hematopoietic endothelial cells (also referred to hemogenic endothelium cells), and a cellular marker of the hematopoietic mesodermal cells is $KDR^+PDGFR\alpha^-$. In some embodiments, the hematopoietic mesodermal cells may be obtained by continuing to culture the mesodermal cells in the mesoderm induction medium (also referred to herein as a hematopoietic mesoderm differentiation medium) supplemented with VEGF and bFGF for about 2 days and assaying for expression of cell markers. The present disclosure also provides cell morphology images of the hematopoietic mesodermal cells, as shown in FIG. 8.

Figure 10:
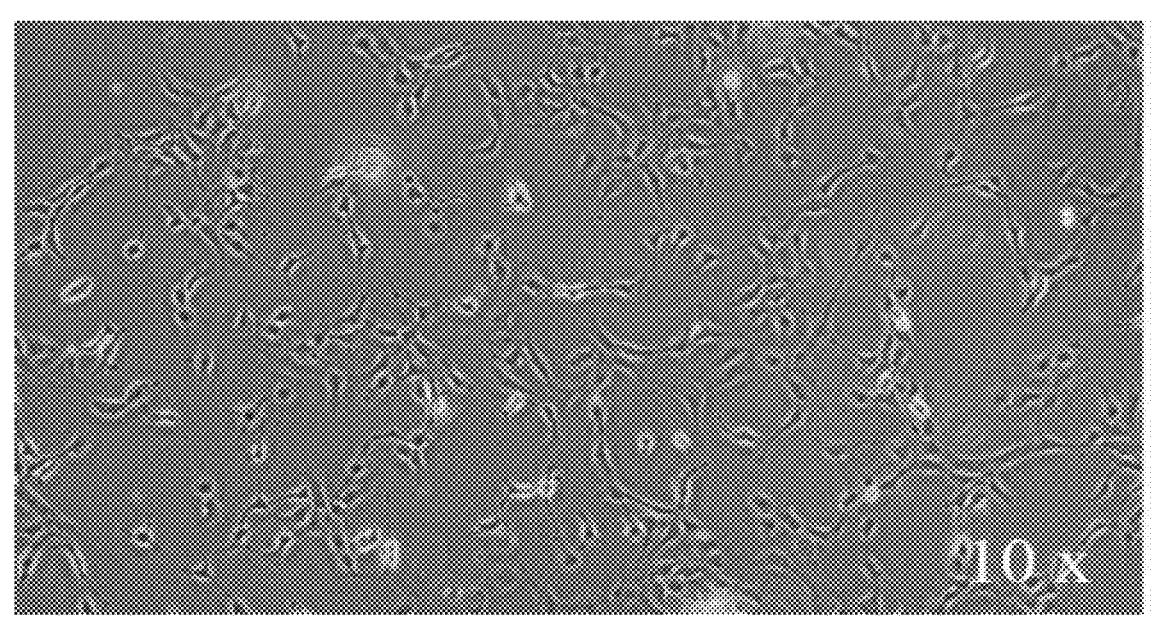
FIG. 10 is cell morphology images of the human pluripotent stem cells (hiPS-001-5-LHHRE) induced to differentiate into the hematopoietic endothelial cells (Day4) at the different magnifications according to some embodiments of the present disclosure.
Figure 10:
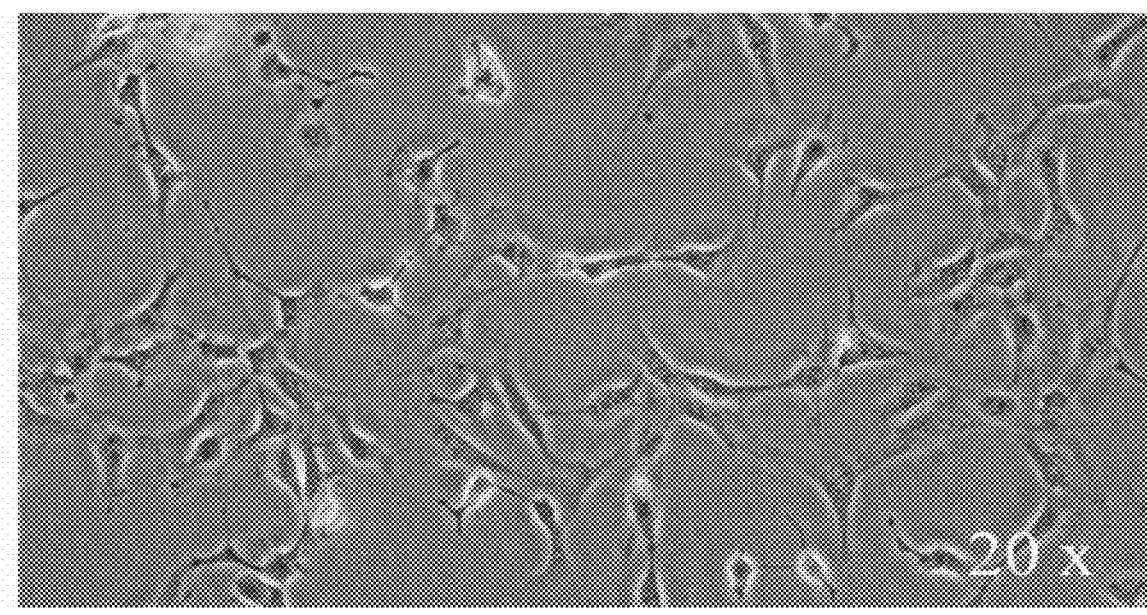
Figure 11:
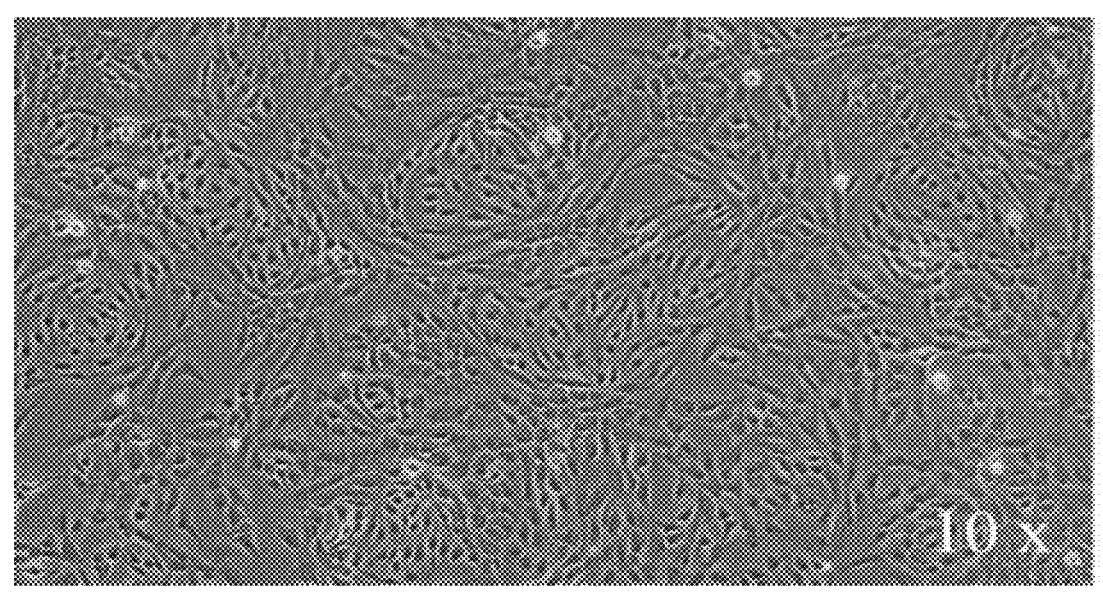
FIG. 11 is cell morphology images of the human pluripotent stem cells (hiPS-001-5-LHHRE) induced to differentiate into the hematopoietic endothelial cells (Day6) at the different magnifications according to some embodiments of the present disclosure.
Figure 11:
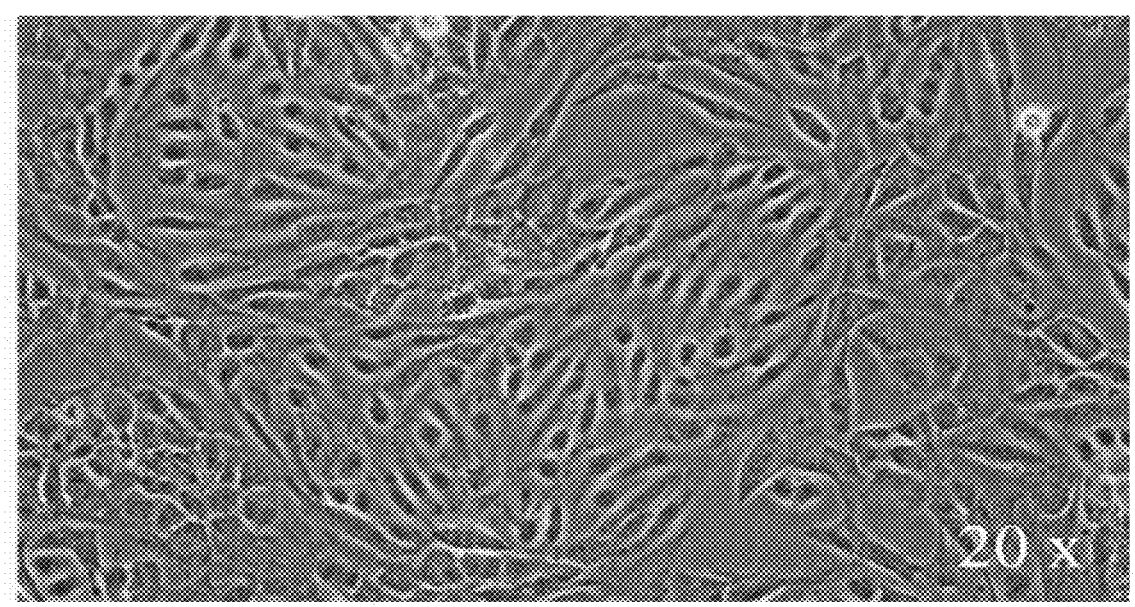

"Hematopoietic endothelial differentiation" in the present disclosure refers to a process of inducing and differentiating the hematopoietic mesodermal cells into the "hematopoietic endothelial cells". Currently, researchers have assumed that the hematopoietic stem cells in vivo are derived from the hematopoietic endothelial cells (see, for example, Hou S, et al. Cell Res (2020), 30, 376-392). In some embodiments, the hematopoietic endothelial cells are obtained by continuing to culture the hematopoietic mesodermal cells in the mesoderm induction medium supplemented with VEGF, bFGF, SCF, IL-3, TPO, Flt-3L, and BMP4 (also referred to herein in the present disclosure as the hematopoietic endothelial differentiation medium when used for the preparation of the hematopoietic endothelial cells, and also referred to herein in the present disclosure as a hematopoietic endothelial differentiation and endothelial-to-hematopoietic transition medium when used for the preparation of the hematopoietic stem cells) for several days (e.g., 3 to 12 days or more, e.g., 4, 5, 6, 7, 8, 9, 10, 11, 12, 13, 14 days, etc.). Markers CD34, KDR, and CD144 may be used to isolate or identify the hematopoietic endothelial cells. The present disclosure also provides cell morphology images of the hematopoietic mesodermal cells, as shown in FIG. 10 and FIG. 11.

"Endothelial-to-hematopoietic transition" in the present disclosure refers to a process of transforming the hematopoietic endothelial cells into the hematopoietic stem cells or hematopoietic stem and progenitor cells. The process ultimately produces the hematopoietic stem cells with therapeutic applications, including long-term hematopoietic stem cells (LT-HSCs). The HSCs or the hematopoietic stem and progenitor cells may be isolated or identified by cellular markers, e.g., CD34, CD45, CD90, CD45RA, EPCR, or ITGA3. In some embodiments, the LT-HSCs are identified by markers CD34, CD90, EPCR, and ITGA3. In some embodiments, short-term hematopoietic stem cells (ST-HSCs) are characterized by $CD34^+EPCR^+CD90^+ITGA3^-$, and the ST-HSCs are maintained in mice for 3-6 months. In some embodiments, the LT-HSCs are characterized by the $CD34^+EPCR^+CD90^+ITGA3^+$. The ITGA3 is a functional marker for in vitro expanded human long-term hematopoietic stem cells. For example, Tomellini et al. demonstrated that the ITGA3 is essential for maintaining activity of long-term stem cells in vivo, ITGA3 expression is functionally required for long-term engraftment of cord blood (CB) cells, and the ITGA3 is a reliable marker for HSCs cultured in CB samples, improving the accuracy of prospective HSC identification and enabling differentiate ST-HSCs and pluripotent LT-HSCs in the expanded CB cultures (see Tomellini, et al. *Integrin-α3 Is a Functional Marker of Ex Vivo Expanded Human Long-Term Hematopoietic Stem Cells. Cell Rep.* 2019; 28(4):1063-1073).

"Promoter" is a DNA sequence that is recognized, bound, and transcribed by RNA polymerase, which contains conserved sequences required for specific binding by the RNA polymerase and for transcription initiation, mostly located upstream of the transcription start site of structural genes; and the promoter itself is not transcribed. In some embodiments, the promoter includes, but is not limited to, CMV, EF1A, CAG, CBh, SFFV promoter.

"Inducible promoter" refers to a promoter sequence including at least one transcriptional regulatory sequence. When specific transcription factors bind to the transcriptional regulatory sequence, they may initiate or promote the promoter to transcribe its downstream DNA sequence. The transcriptional regulatory sequence and the promoter may or may not be naturally present in the transcriptional regulatory sequence of the same gene and may be referred to as a naturally inducible promoter or an artificially inducible promoter, respectively. In some embodiments, the inducible promoter is a tetracycline-inducible promoter (artificially inducible promoter). For example, the tetracycline-inducible promoter includes a minimal CMV promotor (PminCMV) and a Tet-responsive element (TRE). In the presence of doxycycline (DOX), reverse tetracycline transcriptional activator (rtTA) binds to the DOX and then binds to TRE, which activates PminCMV to promote gene expression. In the absence of the DOX, the rtTA does not bind to the TRE, and the PminCMV itself may not initiate the gene expression. Thus, the activity of the inducible promoter may be controlled by whether to add the DOX when the rtTA is simultaneously expressed in the cell (either by using an additional expression vector, or by using a host cell that already incorporates the rtTA coding sequence). It is appreciated by those skilled in the art that, in addition to the tetracycline-inducible promoter, other inducible expression systems may be employed to accomplish the purposes of the present disclosure, e.g., an ecdysone-inducible system, Cumate, a rapamycin-inducible system, and other expression systems commonly used in the art.

"Operably linked to the inducible promoter" refers to a mode of connection between a regulatory sequence inducible promoter and a regulatory target of the regulatory sequence inducible promoter, enabling the regulatory sequence inducible promoter to function on the regulatory target of the regulatory sequence inducible promoter. For example, the promoter being operably linked to a target gene refers to that the promoter may drive the onset of transcription of the target gene from the exact start site.

The term "vector" refers to a nucleic acid molecule that is engineered to contain a target polynucleotide (e.g., a coding sequence of a target protein) or a nucleic acid molecule (e.g., a nucleic acid, a plasmid, or a virus, etc.) that is replicated in the host cell. The vector may include one or more of the following components: a replication origin, one or more regulatory sequences (e.g., at least one of a promoter and enhancer) that regulate the expression of the target polynucleotide, and one or more selectable marker genes (e.g., antibiotic resistance genes and genes that are used in colorimetric analyses, such as beta-galactose). The term "expression vector" refers to a vector used to express the target protein in the host cell. A plasmid vector is typically used for transient expression of the target protein in the cell, whereas a viral vector, such as a lentiviral vector, is used for stable expression in the cell.

Referring to a nucleic acid sequence encoding the protein, "expression" refers to at least one of transcription and translation of the nucleic acid sequence encoding the protein. Expression may be at a basal level, i.e., the level at which a particular gene is normally expressed in a particular cell. Expression may also be at a supra-level, i.e., overexpression, where the count of mRNA or protein produced is typically several times that of the basal level, for example, 5 times, 10 times, 20 times, 50 times, 100 times, 200 times, 500 times, 1000 times, or more. Introducing an exogenously nucleic acid sequence (including an expression cassette of the nucleic acid sequence encoding the target protein) into the host cell (e.g., a stem cell) is one way of enabling overexpression of the target protein in a corresponding host cell. A strong promoter or an inducible strong promoter set in the expression cassette can further enhance expression levels.

Embodiments of the present disclosure provide a method for preparing the hematopoietic endothelial cells, including first constructing the iPSCs that induce the expression of the transcription factors LCOR, HOXA9, HOXA5, RUNX1, and ERG and inducing the expression of the transcription factors during an induction process (in particular, at least one of hematopoietic endothelial differentiation and endothelial-to-hematopoietic transition processes) of the iPSCs into the hematopoietic stem cells, thereby increasing yield or efficiency of the hematopoietic endothelial cells. In some embodiments of the present disclosure, inducing the expression of the transcription factors at specific time periods can significantly increase the proportion (or yield) of the hematopoietic endothelial cells in a culture. FIG. 1 is a flowchart of the differentiation of the human pluripotent stem cells (hiPS-001-5-LHHRE) to the long-term repopulating hematopoietic stem cells according to some embodiments of the present disclosure, from Day−1 to Day0, it refers to the formation of single cells and a TeSR-E8 medium is used, with a cell density of 8,000 cells/cm², and 10 µM Y-27632 is added; from Day0 to Day1, a mesoderm induction medium including 9 µM CHIR 99021 (CHIR) is used; from Day1 to Day3, a hematopoietic mesoderm differentiation medium including 20 ng/mL VEGF and 20 ng/mL bFGF is used; from Day3 to Day6, a hematopoietic endothelial differentiation and endothelial-to-hematopoietic transition medium including 20 ng/mL VEGF, 20 ng/mL bFGF, 50 ng/mL SCF, 10 ng/mL IL-3, 30 ng/mL TPO, 10 ng/mL Flt-3L, and 10 ng/mL BMP4 is used. Cell passage is performed on Day3 at a cell inoculation density of $2 \times 10^4$ cells/cm$^2$ with an additional 10 μM of Y-27632, and the medium is changed after 24 h to remove the Y-27632. From Day6 to Day12, the hematopoietic endothelial differentiation and endothelial-to-hematopoietic transition medium including 20 ng/mL VEGF, 20 ng/mL bFGF, 50 ng/mL SCF, 10 ng/mL IL-3, 30 ng/mL TPO, 10 ng/mL Flt-3L, 10 ng/mL BMP4, and 5 μg/mL DOX is used, and the DOX induces overexpression of LCOR, HOXA9, HOXA5, RUNX1, and ERG. Thereafter, fresh hematopoietic endothelial differentiation and endothelial-to-hematopoietic transition medium including DOX is changed every two days until Day12. In some embodiments, the expression of the above-described transcription factors is induced (i.e., the DOX is added to the culture medium) from days 1 to 4 (corresponding to Day3-Day6 in the FIG. 1) of the hematopoietic endothelial differentiation. In some embodiments, the expression of the above-described transcription factors is induced from days 4 to 7(corresponding to Day6-Day9 in the FIG. 1) of the hematopoietic endothelial differentiation. In some embodiments, the expression of the above-described transcription factors is induced from day 4 (corresponding to Day 6 in the FIG. 1) onwards of the hematopoietic endothelial differentiation. The production of the hematopoietic endothelial cells may be identified by at least one of observation of cell morphology and detection of cell markers. For example, a cell morphology observation and a marker detection may be performed on Day 2 (corresponding to Day 4 in the FIG. 1) of the hematopoietic endothelial differentiation. In some embodiments, when referring to performing the cell morphology observation or the marker detection, the corresponding time such as Day4 usually refers to the beginning of that day, or it may be before a specific treatment (e.g., inoculation, change of medium, etc.) is performed on the cultured cells on that day. It is appreciated by those skilled in the art that for a culture process of at least one of the hematopoietic endothelial differentiation and the endothelium-to-hematopoietic transitions taking several days, differences in culture time of a few hours or a dozen hours usually do not result in significant changes in the cell morphology or markers. In some embodiments, the method for preparing the hematopoietic endothelial cells includes: (a) providing the hematopoietic mesodermal cells or the cell culture including the hematopoietic mesodermal cells; (b) culturing the hematopoietic mesodermal cells or the cell culture including the hematopoietic mesodermal cells in a hematopoietic endothelial differentiation medium; and (c) inducing the hematopoietic mesodermal cells to express the transcription factors LCOR, HOXA9, HOXA5, RUNX1, and ERG. In some embodiments, although the process of preparing the hematopoietic endothelial cells is described by a way of a step-by-step process, step (c) (inducing the hematopoietic mesodermal cells to express the transcription factors LCOR, HOXA9, HOXA5, RUNX1, and ERG) is not performed after step (b), but rather is performed during the culture process of the step (b). For example, the step (b) is performed for 10 days, and the step (c) is performed on days 4to 7 of the culturing in the step (b).

Embodiments of the present disclosure provide a method for preparing the hematopoietic stem cells, including first constructing the iPSCs that induce the expression of the transcription factors LCOR, HOXA9, HOXA5, RUNX1, and ERG, and controlling the expression of the transcription factors at specific time periods during an induction process of the iPSCs into the hematopoietic stem cells, thereby increasing the yield or efficiency of the hematopoietic stem cells. In some embodiments of the present disclosure, inducing the expression of these transcription factors at specific time periods can significantly increase the proportion (or yield) of the hematopoietic stem cells in the culture. In some embodiments, the expression of the above-described transcription factors is induced (i.e., DOX is added to the culture medium) on days 4 to 10 (corresponding to Day6-Day12 in the FIG. 1) of the hematopoietic endothelial differentiation. In some embodiments, the expression of the above-described transcription factors is induced from day 4 (corresponding to Day 6 in the FIG. 1) of the hematopoietic endothelial differentiation. The production of the hematopoietic stem cells (including the hematopoietic stem and progenitor cells or the LT-HSCs) may be identified by at least one of the observation of the cell morphology and the detection of the cell markers. In some embodiments, the method for preparing the hematopoietic stem cells includes: (1) providing hematopoietic mesodermal cells or a cell culture including the hematopoietic mesodermal cells; (2) culturing the hematopoietic mesodermal cells or the cell culture including the hematopoietic mesodermal cells in the hematopoietic endothelial differentiation and endothelial-to-hematopoietic transition medium; and (3) inducing the hematopoietic mesodermal cells to express the transcription factors LCOR, HOXA9, HOXA5, RUNX1, and ERG. In some embodiments, step (3) is not required to be performed after step (2), but rather is performed during the culturing of the step (2).

In some embodiments of the present disclosure, the whole process from the iPSCs to the hematopoietic stem cells is described in detail, as shown in FIG. 1. The process of differentiation of the human pluripotent stem cells to the hematopoietic cells mainly includes monolayer cell formation, mesoderm induction, hematopoietic mesoderm differentiation, hematopoietic endothelial differentiation and endothelial-to-hematopoietic transition. The hematopoietic mesodermal cells and the hematopoietic endothelial cells are not isolated and purified after induction of the hematopoietic mesodermal cells. Instead, the final hematopoietic stem cells (including the long-term hematopoietic stem cells) are obtained only by changing the composition of the culture medium (the addition of DOX). The effects of adding DOX at different times on the production of the hematopoietic endothelial cells and the production of the hematopoietic stem cells are investigated in this process. Obviously, a person skilled in the art is capable of preparing the hematopoietic endothelial cells from the mesodermal cells or the hematopoietic mesodermal cells, or preparing the hematopoietic stem cells from the mesodermal cells, the hematopoietic mesodermal cells, or the hematopoietic endothelial cells based on embodiments of the present disclosure. As long as the expression of the above-described transcription factors is induced at a corresponding time, these modified technical solutions shall also be included within the scope of the present disclosure.

The literature published by Sugimura et al. (Sugimura, R., J ha, D., Han, A. et al. *Hematopoietic stem and progenitor cells from human pluripotent stem cells. Nature* 545, 432-438 (2017)) reported that inducing the expression of LCOR, HOXA9, HOXA5, RUNX1, and ERG (referred to as LHHRE) in mice can transform CD34$^+$ cells into the hematopoietic stem and progenitor cells (but CD34 is expressed in both the hematopoietic endothelial cells and endothelial cells, so that the CD34$^+$ cells in the literature could also be the endothelial cells); at the same time, CD34$^+$CD43$^+$CD45$^+$ cells obtained by inducing the hematopoietic endothelial cells to express the LHHRE in vitro have multilineage transplantation potential. All of the above experiments involved the re-induction of the LHHRE gene in vivo, and thus it is possible that the above experiments indicate that the in vivo environment is a critical factor for the generation of the hematopoietic stem and progenitor cells from LHHRE induction. There is no direct evidence in this literature that CD34$^+$CD43$^+$CD45$^+$ cells derived from the LHHRE expression in vitro are CD34$^+$EPCR$^+$CD90$^+$ITGA3$^+$ long-term repopulating hematopoietic stem cells. In some embodiments of the present disclosure, a serum-free differentiation system and an easy-to-manipulate differentiation process are established. By stage-specifically regulating key signaling pathways associated with the hematopoietic stem cells development, and using the Tet-on tetracycline-induced expression system to stage-specifically induce overexpression of core transcription factors LCOR, HOXA9, HOXA5, RUNX1, and ERG associated with the developmental process of the hematopoietic stem cells, it can achieve efficient differentiation from the human pluripotent stem cells to CD34$^+$EPCR$^+$CD90$^+$ITGA3$^+$ long-term repopulating hematopoietic stem cells in vitro, and these hematopoietic stem cells have differentiation potential of different hematopoietic colonies. Meanwhile, it is found that LCOR, HOXA9, HOXA5, RUNX1, and ERG can promote the generation of CD34$^+$KDR$^+$CD144$^+$ hematopoietic endothelial cells. The literature published by Sugimura et al. only indicated that the expression of the LHHRE in mice could transform CD34$^+$ cells into the hematopoietic stem and progenitor cells, which has a multi-lineage hematopoietic differentiation potential. While in vitro expression of LHHRE transforms CD34$^+$ cells into CD34$^+$CD43$^+$CD45$^+$ cells and injecting the cells into mice and continuing to induce LHHRE expression can enable cells have multi-lineage hematopoietic differentiation potential. The literature involves the in vivo induction and expression of the LHHRE gene, which may potentially indicate that the in vivo environment is a key factor in achieving hematopoietic stem and progenitor cell transformation, but does not indicate that LHHRE can achieve the induced differentiation of CD34$^+$EPCR$^+$CD90$^+$ITGA3$^+$ long term repopulating hematopoietic stem cells in vitro. Meanwhile, the literature does not report that the effects of LHHRE on the generation of the CD34$^+$KDR$^+$CD144$^+$ hematopoietic endothelial cells.

Embodiments of the present disclosure establish a serum-free differentiation system and an easy-to-operate differentiation process. By stage-specifically regulating the key signaling pathways associated with the hematopoietic stem cells development, and using the Tet-on tetracycline-induced expression system to stage-specifically inducing the overexpression of the core transcription factors LCOR, HOXA9, HOXA5, RUNX1, and ERG associated with the developmental process of the hematopoietic stem cells, it can achieve efficient differentiation from the human pluripotent stem cells to the CD34$^+$EPCR$^+$CD90$^+$ITGA3$^+$ long-term repopulating hematopoietic stem cells in vitro. Meanwhile, it is found that LCOR, HOXA9, HOXA5, RUNX1, and ERG can promote the generation of the CD34$^+$KDR$^+$CD144$^+$ hematopoietic endothelial cells. The present disclosure extends the method for in vitro differentiation of the human pluripotent stem cells into the long-term repopulating hematopoietic stem cells and the hematopoietic endothelial cells, which may provide a new source of the hematopoietic stem cells for future clinical applications and research.

The technical solutions of the present disclosure will be described in further detail below in connection with specific embodiments. It should be understood that the following embodiments are only exemplary for illustrating and explaining the present disclosure and should not be construed as a limitation on the scope of protection of the present disclosure. Any technology realized based on the foregoing contents of the present disclosure is covered by the scope of protection intended by the present disclosure.

EMBODIMENTS

Reagents

Reagent information was shown in Table 1.

TABLE 1

| Reagent Information | | | | | |
|---|---|---|---|---|---|
| Reagent Code | Reagent Name | Production Company | Catalog Number | Final Concentration | Storage Conditions |
| TeSR-E8 Medium | TeSR ™-E8 ™ Basal Medium | Stemcell | 05991 | 1× | −20° C. freezer |
| | TeSR ™-E8 ™ 25 × Supplement | Stemcell | 05992 | 1× | −20° C. freezer |
| | Penicillin-Streptomycin | Gibco | 15140163 | 1% | −20° C. freezer |
| Mesoderm Induction Medium | STEMdiff ™ APEL ™2 Medium | Stemcell | 05275 | 1× | −20° C. freezer |
| | CHIR-99021 | Selleck | S2924 | 9 µM | −20° C. freezer |
| | Penicillin-Streptomycin | Gibco | 15140163 | 1× | −20° C. freezer |
| Hematopoietic Mesoderm Differentiation Medium | STEMdiff ™ APEL ™2 Medium | Stemcell | 05275 | 1× | −20° C. freezer |
| | Recombinant Human VEGF165 | Peprotech | AF-100-20 | 20 ng/mL | −80° C. freezer |
| | Recombinant Human FGF - basic | Peprotech | AF-100-18B | 20 ng/mL | −80° C. freezer |

TABLE 1-continued

| | | | | | |
|---|---|---|---|---|---|
| | | | Reagent Information | | |
| Reagent Code | Reagent Name | Production Company | Catalog Number | Final Concentration | Storage Conditions |
| | Penicillin-Streptomycin | Gibco | 15140163 | 1% | −20° C. freezer |
| Hematopoietic Endothelial Differentiation and Endothelium - To- Hematopoietic Transition Medium | STEMdiff ™ APEL ™2 Medium | Stemcell | 05275 | 1× | −20° C. freezer |
| | Recombinant Human VEGF165 | Peprotech | AF-100-20 | 20 ng/mL | −80° C. freezer |
| | Recombinant Human FGF-basic | Peprotech | AF-100-18B | 20 ng/mL | −80° C. freezer |
| | Recombinant Human BMP-4 | Peprotech | 120-05ET | 10 ng/mL | −80° C. freezer |
| | Recombinant Human IL-3 | Peprotech | AF-200-03 | 10 ng/mL | −80° C. freezer |
| | Recombinant Human TPO | Peprotech | AF-300-18 | 30 ng/mL | −80° C. freezer |
| | Recombinant Human Flt-3L | Peprotech | AF-300-19 | 10 ng/mL | −80° C. freezer |
| | Recombinant Human SCF | Peprotech | 300-07 | 50 ng/mL | −80° C. freezer |
| | Penicillin-Streptomycin | Gibco | 15140163 | 1% | −20° C. freezer |
| TrypLE Working Solution | TrypLE ™ Express Enzyme (1×), No Phenol Red | Gibco | 12604021 | 0.5× | 4° C. freezer |
| | DPBS, No Ca, No Mg | HyClone | SH30028.02 | — | 4° C. freezer |
| Digestive Termination Solution | DMEM/F-12 with HEPES | Gibco | 11320033 | — | 4° C. freezer |
| | CellMax Superior fetal bovine serum | CellMax | SA211.02 | 10% | −20° C. freezer |
| Wash Reagent Buffer A | DPBS, No Ca, No Mg | HyClone | SH30028.02 | — | 4° C. freezer |
| | CellMax Superior fetal bovine serum | CellMax | SA211.02 | 10% | −20° C. freezer |
| Pore-forming Reagent Buffer B | DPBS, No Ca, No Mg | HyClone | SH30028.02 | — | 4° C. freezer |
| | CellMax Superior fetal bovine serum | CellMax | SA211.02 | 10% | −20° C. freezer |
| | Triton X-100 | Solarbio | T8200 | 0.4% | Room Temperature (RT) |
| Other Reagent | 4% Paraformaldehyde | Leagen | DF0135 | — | RT |
| | Matrigel | Corning | 354277 | — | −20° C. freezer |
| | Doxycycline | Selleck | S4163 | 5 µg/mL | −20° C. freezer |
| | Y-27632 | Selleck | S1049 | 10 µM | −20° C. freezer |
| | FITC anti-human CD34 Antibody | Biolegend | 393006 | — | 4° C. freezer |
| | APC anti-human KDR Antibody | Biolegend | 304037 | — | 4° C. freezer |
| | APC anti-human CD45 Antibody | BD biosciences | 555482 | — | 4° C. freezer |
| | PE anti-human PDGFRa Antibody | Biolegend | 323506 | — | 4° C. freezer |
| | Alexa Fluor 488 anti-human Brachyury Antibody | R&D system | IC2085G | — | 4° C. freezer |
| | APC anti-human CD49c (ITGA3) Antibody | Biolegend | 343808 | — | 4° C. freezer |

TABLE 1-continued

| | | | Reagent Information | | |
|---|---|---|---|---|---|
| Reagent Code | Reagent Name | Production Company | Catalog Number | Final Concentration | Storage Conditions |
| | PE anti-human CD201 (EPCR) Antibody | Biolegend | 351904 | — | 4° C. freezer |
| | APC anti-human CD201 (EPCR) Antibody | Biolegend | 351906 | — | 4° C. freezer |
| | PerCP/Cyanine 5.5 anti-human CD90 Antibody | Biolegend | 328118 | — | 4° C. freezer |
| | PE anti-human CD90 Antibody | Biolegend | 328110 | — | 4° C. freezer |
| | PerCP anti-human CD45RA Antibody | Biolegend | 304156 | — | 4° C. freezer |
| | PE anti-human CD144 (VE-cadherin) Antibody | Biolegend | 348506 | — | 4° C. freezer |
| | APC anti-human CD235a Antibody | eBioscience | 17-9987-42 | — | 4° C. freezer |

Experimental Methods

Flow Cytometry of Cell Surface Markers

1. Reagents and Antibodies Required for Fluorescence-Activated Cell Sorting (FACS)
    (1) Wash reagent: Buffer A (PBS +4% FBS).
    (2) Directly conjugated primary antibody: FITC anti-human CD34 antibody, APC anti-human KDR antibody, PE anti-human PDGFRα antibody, PE anti-human CD144 antibody, APC anti-human ITGA3 antibody, PE anti-human EPCR antibody, PerCP/Cyanine5.5 anti-human CD90 antibody.
2. Preparation of Samples to be Tested
    1) Preparation of TrypLE working solution: pipetting an appropriate volume of DP BS into a new 15 mL centrifuge tube, adding a corresponding volume of TrypLE stock solution according to a ratio of 1:1, mixing well to obtain the working solution, and pre-heating at 37° C. for 10 min.
    2) Taking differentiated cells from an incubator, aspirating and discarding an original culture medium, adding appropriate volume of the DP BS to wash the cells, and repeating the washing twice (with the volume of DPBS not less than the volume of the original culture medium) for 1 min each time (when washing, leaving the DBPS in a plate/bottle for 30-45 s before aspirating).
    3) Adding TrypLE working solution (1 mL TrypLE working solution per each well of a 6-well culture plate) to make the TrypLE working solution cover the bottom of the plate uniformly, and placing the plate in the incubator for 2-5 min, and observing under the microscope until the cells shrink, become round, and disperse.
    4) Gently tapping the culture flask/plate to detach the cells from the bottom of the plate, then gently blowing several times with a pipette, finally adding an equal volume of Buffer A to terminate the digestion, and taking $1 \times 10^6$ cells after cell counting. (for suspension cells, the cell digestion step is not required, and the suspension cells are directly collected for subsequent operations).

5) After balancing, centrifuging at 200 g for 5 min, aspirating and discarding the supernatant after centrifugation, flicking the bottom of the centrifuge tube to make the cells well dispersed, resuspending the cells by adding appropriate volume of Buffer A, centrifugating at 200 g for 5 min, and discarding the supernatant.
6) Washing the cells twice with Buffer A, 3 mL of the Buffer A each time, centrifuging at 200 g for 5 min and discarding the supernatant.
7) Incubation of the directly conjugated primary antibody: after resuspending the cells with 100 μL of the Buffer A, adding 1 test of directly conjugated primary antibody to each tube and incubating at 4° C. for 30 min, and flicking the tube every 10 min to fully bind the antibody to the cells.
8) Washing the cells 3 times with the Buffer A, 3 mL of Buffer A each time, centrifuging at 200 g for 5 min and discarding the supernatant.
9) Resuspending the cells by adding 200 μL of DP BS to each tube and filtering the cells through a filter with a pore size of 70 μm to remove undigested cell clumps, transferring the filtered cell suspension to a 96-well culture plate, storing at 4° C. in the dark, and waiting for the assay.
Note: Hematopoietic mesodermal cells markers KDR and PDGFRα were detected on day 3 of the induction differentiation.

Hematopoietic endothelial cells markers CD34, KDR, and CD144 were detected on days 6 and 9 of the induction differentiation.

Hematopoietic stem and progenitor cells markers CD34 and CD45 were detected on days 9 and 12 of the induction differentiation.

Long-term repopulating hematopoietic stem cells markers CD34, CD90, CD45RA, EPCR, and ITGA3 were detected on day 12 of the induction differentiation.

Flow Cytometry of Intranuclear Markers

1. Reagents and Antibodies Required for FACS
    (1) Wash reagent: Buffer A (PBS+4% FBS).

(2) Pore-forming reagent: Buffer B (PBS+4% FBS+0.4% Triton X-100).

(3) Fixation reagent: PBS+4% paraformaldehyde.

(4) Directly conjugated primary antibody: Human/Mouse Brachyury Alexa Fluor® 488-conjugated Antibody, or the like.

2. Preparation of Samples to be Tested

1) Preparation of the TrypLE working solution: pipetting an appropriate volume of DPBS into a new 15 mL centrifuge tube, adding a corresponding volume of TrypLE stock solution according to a ratio of 1:1, mixing well to obtain the working solution, and pre-heating at 37° C. for 10 min.

2) Taking the differentiated cells from the incubator, aspirating and discarding the original culture medium, adding an appropriate volume of DPBS to wash the cells, and repeating the washing twice (with the volume of DPBS not less than the volume of the original culture medium) for 1 min each time (when washing, leaving the DPBS in the plate/bottle for 30-45 s before aspirating).

3) Adding the TrypLE working solution (1 mL TrypLE working solution per well of a 6-well culture plate) to make the TrypLE working solution cover the bottom of the plate uniformly, and placing the plate in the incubator for 2-5 min, observing under the microscope until the cells shrink, become round, and disperse.

4) Gently tapping the culture flask/plate to detach the cells from the bottom of the plate, then gently blowing several times with a pipette, finally adding an equal volume of Buffer A to terminate the digestion, and taking $1 \times 10^6$ cells after cell counting.

5) After balancing, centrifuging at 200 g for 5 min, aspirating and discarding the supernatant after centrifugation, flicking the bottom of the centrifuge tube to make the cells well dispersed, adding 0.5 mL of PBS+ 4% paraformaldehyde to each tube, flicking the centrifuge tube to make the cells suspended in the paraformaldehyde solution, and then fixing the cells at 4° C. for 15 min, centrifuging at 200 g for 5 min, and discarding the supernatant.

6) Washing the cells 3 times with Buffer B including 0.4% Triton X-100 to perforate the cell membrane, using 3 mL of Buffer B each time, centrifuging at 200 g for 5 min and discarding the supernatant.

7) Incubation of the directly conjugated primary antibody: after resuspending the cells with 100 μL of Buffer B, adding 1 test of directly conjugated primary antibody to each tube and incubating at 4° C. for 30 min, and flicking the centrifuge tube every 10 min to fully bind the antibody to the cells.

8) Washing the cells 3 times with Buffer A, using 3 mL of Buffer A each time, centrifuging at 200 g for 5 min and discarding the supernatant.

9) Resuspending the cells by adding 200 μL of DP BS to each tube and filtering the cells through a filter with a pore size of 70 μm to remove undigested cell clumps, transferring the filtered resuspended cells to a 96-well culture plate, storing at 4° C. in the dark, and waiting for the assay.

Note: The mesodermal cells marker Brachyury (T) was detected on day 1 of the induction differentiation.

Flow Cytometry Analysis

The brief steps were as follows:

1) Turning on the flow cytometer Guava easyCyte HT and the computer.

2) Setting up the flow cytometer; opening the flow cytometry software and setting up various parameters.

3) After the machine enters a "Ready" state, cleaning the machine.

4) Firstly, through the isotype control sample, setting the voltages and gains of forward scatter (FSC) and side scatter (SSC) so that the discrete cell populations are located in the appropriate position in the quadrants, generally with cell debris in the lower left quadrant and larger cell clumps in the upper right quadrant. Circling the target cell population, setting Gate, and proceeding to the next step of analysis.

5) Selecting the appropriate detection channel according to the fluorochrome conjugated the antibody. Adjusting voltages and compensations of the corresponding channel to clearly distinguish negative and positive cell populations, and then detecting the experimental samples sequentially.

6) When detecting is complete, cleaning the flow cytometer and turning off the flow cytometer and computer.

Embodiment 1 Construction of the Stable Cell Line hiPS-001-5-LHHRE

Figure 2A:
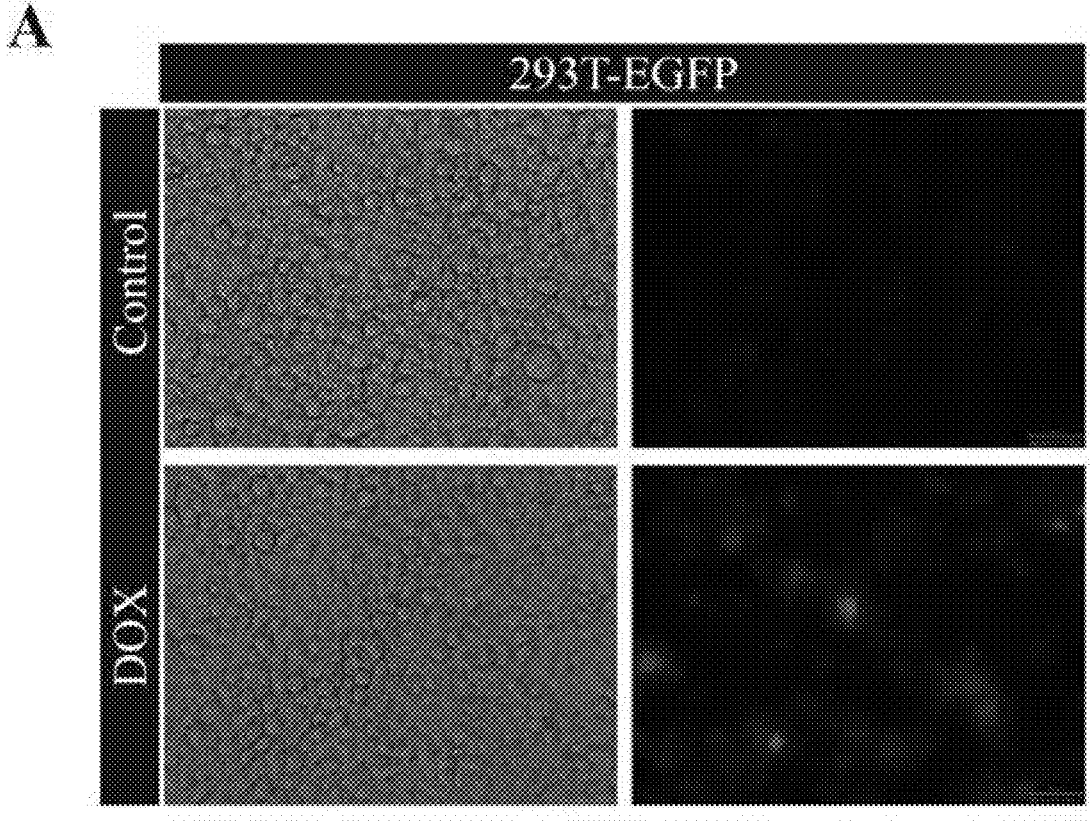
FIGS. 2A-2G illustrate a validation of induced expression and determination of drug screening dose of a Tet-on tetracycline-inducible expression system according to some embodiments of the present disclosure.
Figure 2B:
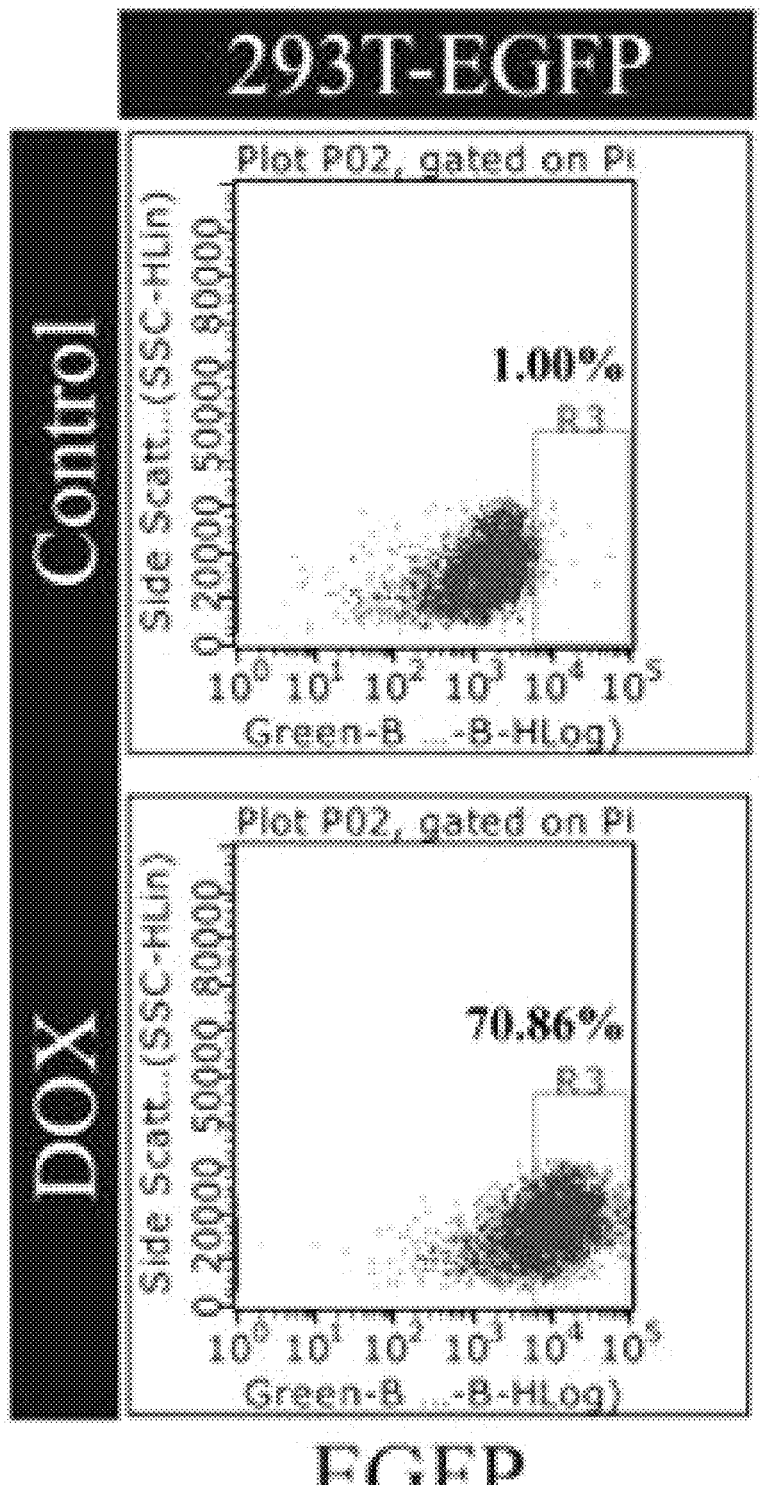
Figure 2C:
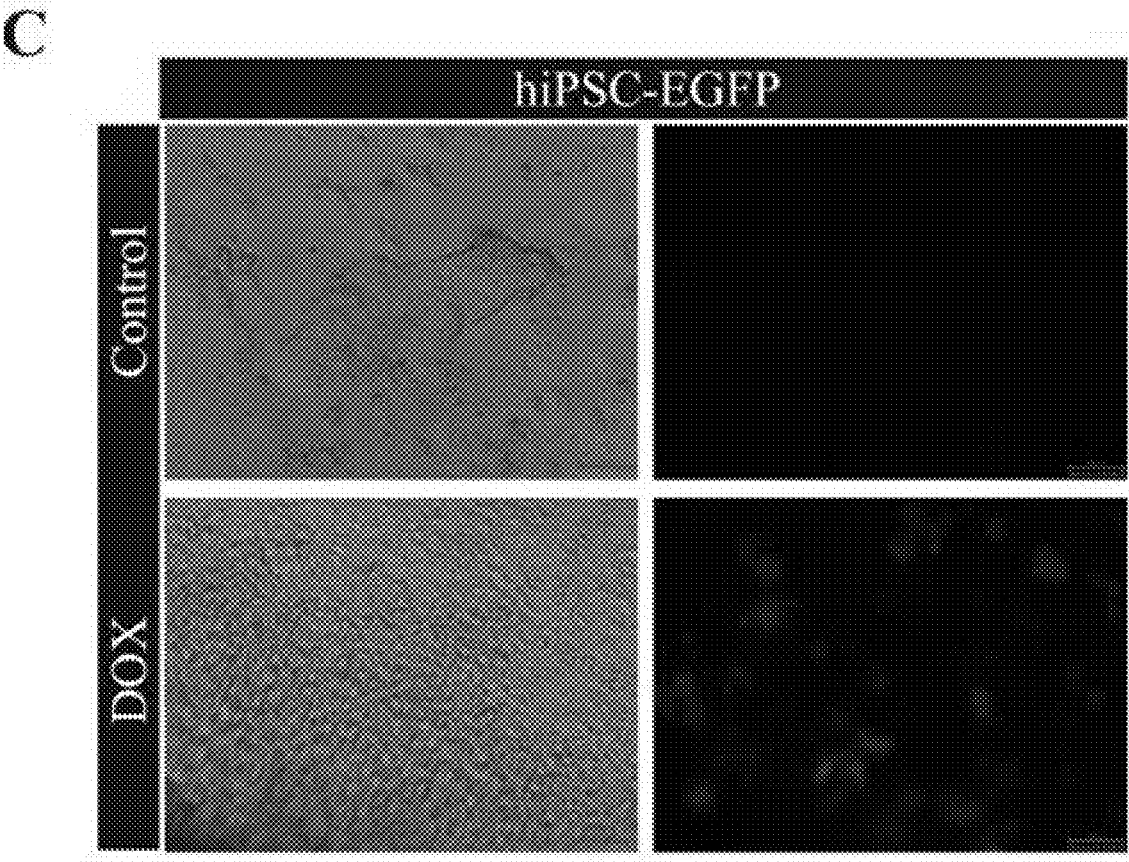
Figure 2D:
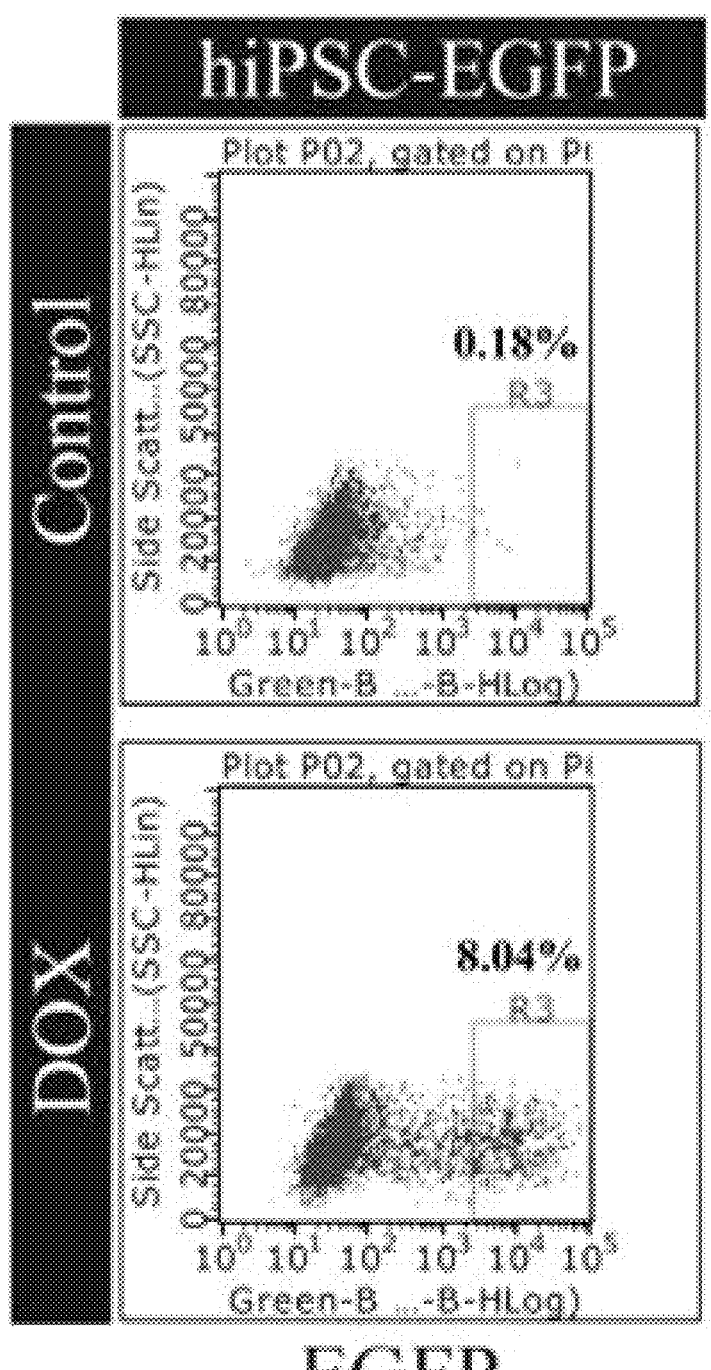

In order to realize the regulation of the expression time of the transcription factors, this embodiment constructed the Tet-on tetracycline-inducible expression system. First, the reliability of the Tet-on tetracycline-inducible expression system was verified. As shown in the fluorescence images of FIG. 2A and FIG. 2C, 72 h after transient transfection of pLenti-EF1α-rtTA-IRES-PuroR and TetO-FUW-EGFP-EF1α-NeoR plasmids in 293T (from ATCC) and hiPSCs (prepared as described in CN113462638A) cells, the control group (Control without DOX) indicates no EPGF expression, while the experimental group (DOX) treated with 5 μg/mL Doxycycline indicates significant induction of EGFP expression. As shown in the flow cytometry analysis of FIG. 2B and FIG. 2D, in the 293T cells, the proportion of EGFP⁺ cells in the DOX experimental group is 70.86%, whereas the proportion of EGFP⁺ cells in the Control group is only 1.00%; in hiPSCs, the proportion of EGFP⁺ cells in the DOX experimental group is 8.04%, while the proportion of EGFP⁺ cells in the Control group is only 0.18%. The difference in the proportion of EGFP⁺ cells in 293T and hiPSCs cells is caused by the difference in the efficiency of plasmid transfection of different cell types. The above experimental results indicate that in 293T and hiPSCs cells, the Tet-on tetracycline-inducible expression system used in the present embodiment can reliably regulate the induced expression of the target gene.

Figure 2E:
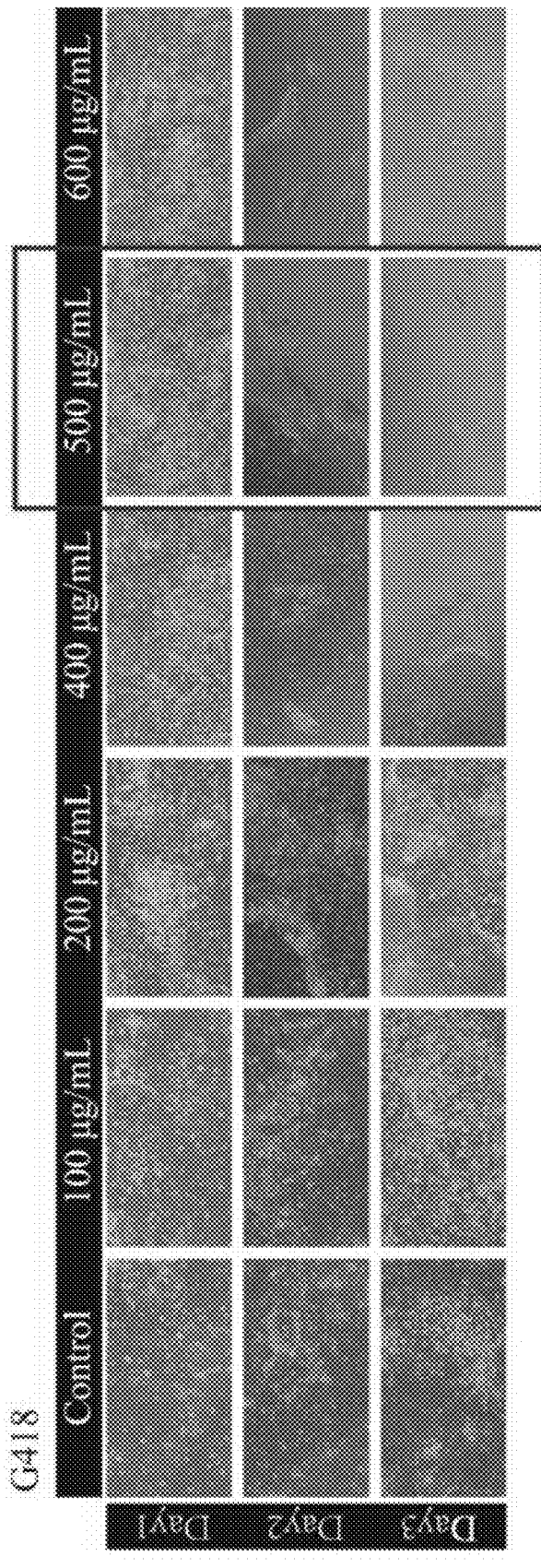
Figure 2F:
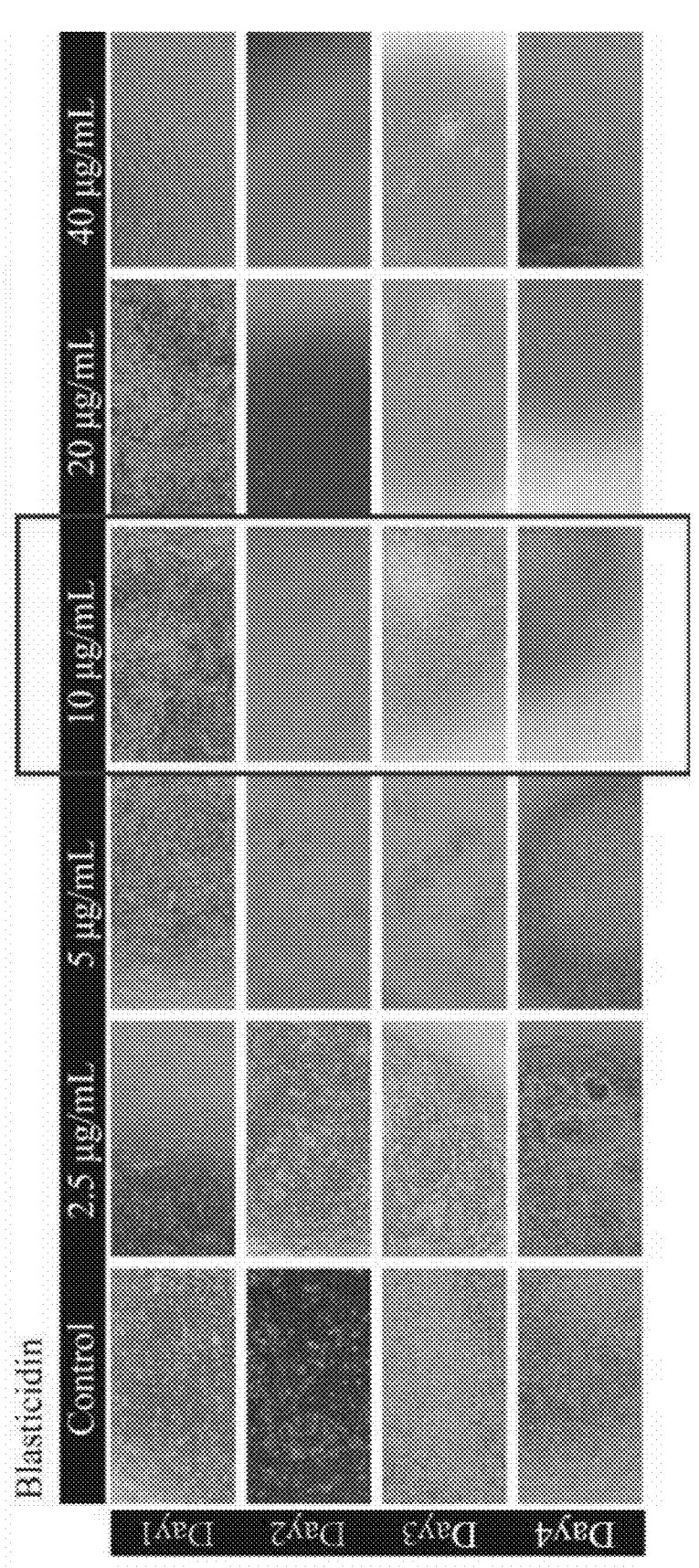
Figure 2G:
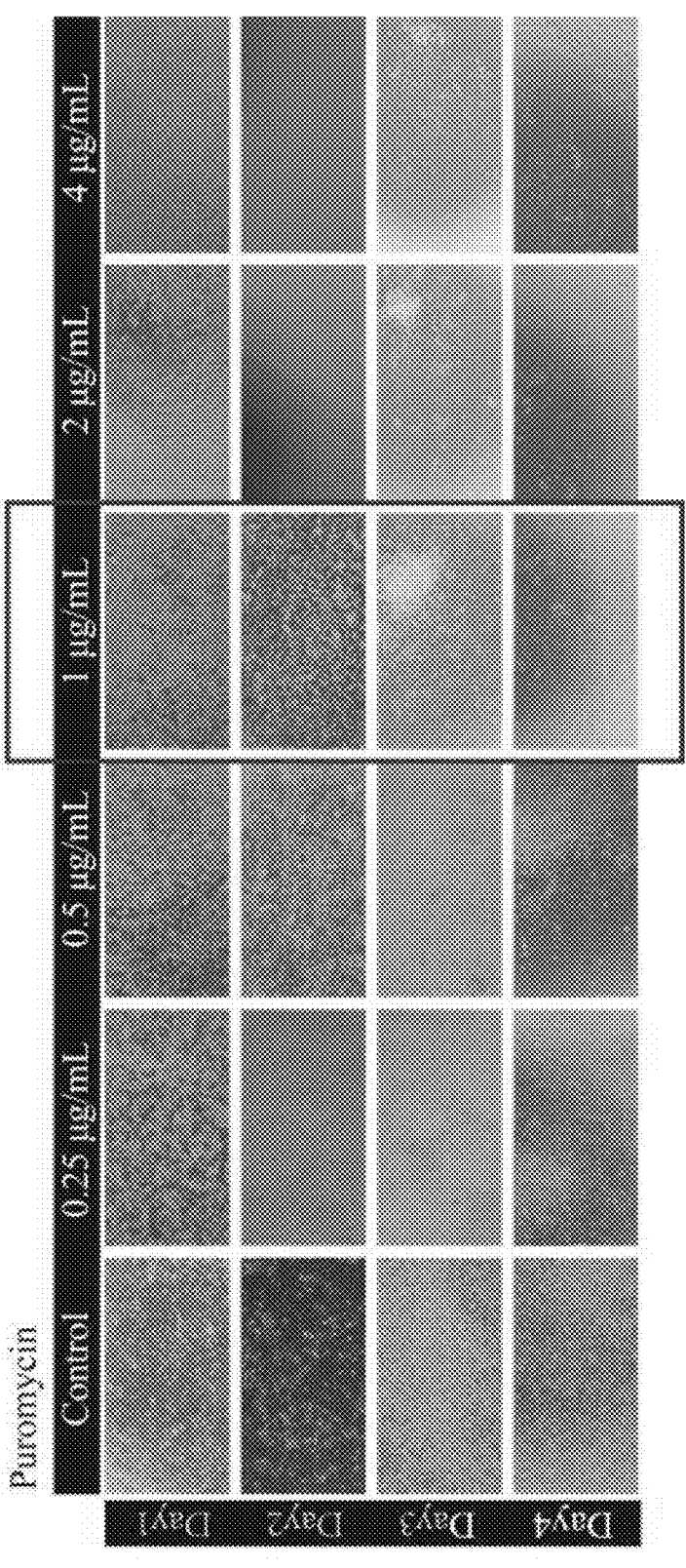

On the basis of the above experiments, the present embodiment utilized lentivirus to construct a stable cell line hiPS-001-5-LHHRE with conditional inducible expression of LHHRE. The following three expression vectors were used to construct this cell line: TetO-FUW-LCOR-HOXA9-HOXA5-EF1α-BSD (with 2A self-cleaving peptide sequences between different proteins), TetO-FUW-RUNX1-ERG-EF1α-NeoR (with 2A self-cleaving peptide sequences between different proteins), and pLenti-EF1a-rtTA-IRES-PuroR, each vector carrying a drug screening resistance gene. In order to determine the appropriate drug screening dose, this embodiment performed drug screening experiments on hiPS-001-5 cells using 0-600 µg/mL G418, 0-40 µg/mL Blasticidin, or 0-4 µg/mL Puromycin, respectively. As shown in FIGS. 2E-2G, the lowest concentrations of drugs that led to the basic death of hipS-001-5 cells after 3-4 days of drug screening are 500 µg/mL G418, 10 µg/mL Blasticidin, and 1 µg/mL Puromycin, respectively. The present embodiment utilized the above concentrations of G418, Blasticidin, and Puromycin to screen the cells 72 h after transfection with the virus, thereby obtaining the stable transfected cell line hiPS-001-5-LHHRE.

The hiPS-001-5 is a human induced pluripotent stem cells line (IP SC) constructed independently in the present disclosure, named hiPS-001-5 cells before the introduction of the LHHRE gene and hiPS-001-5-LHHRE cells after the introduction of the LHHRE gene, respectively. The IPSC of the present disclosure may be prepared by the preparation method in patent application CN201910110768.7 or patent application CN202110733296.8 and may also be prepared by a method known in the art or a commercialized kit.

Figure 3A:
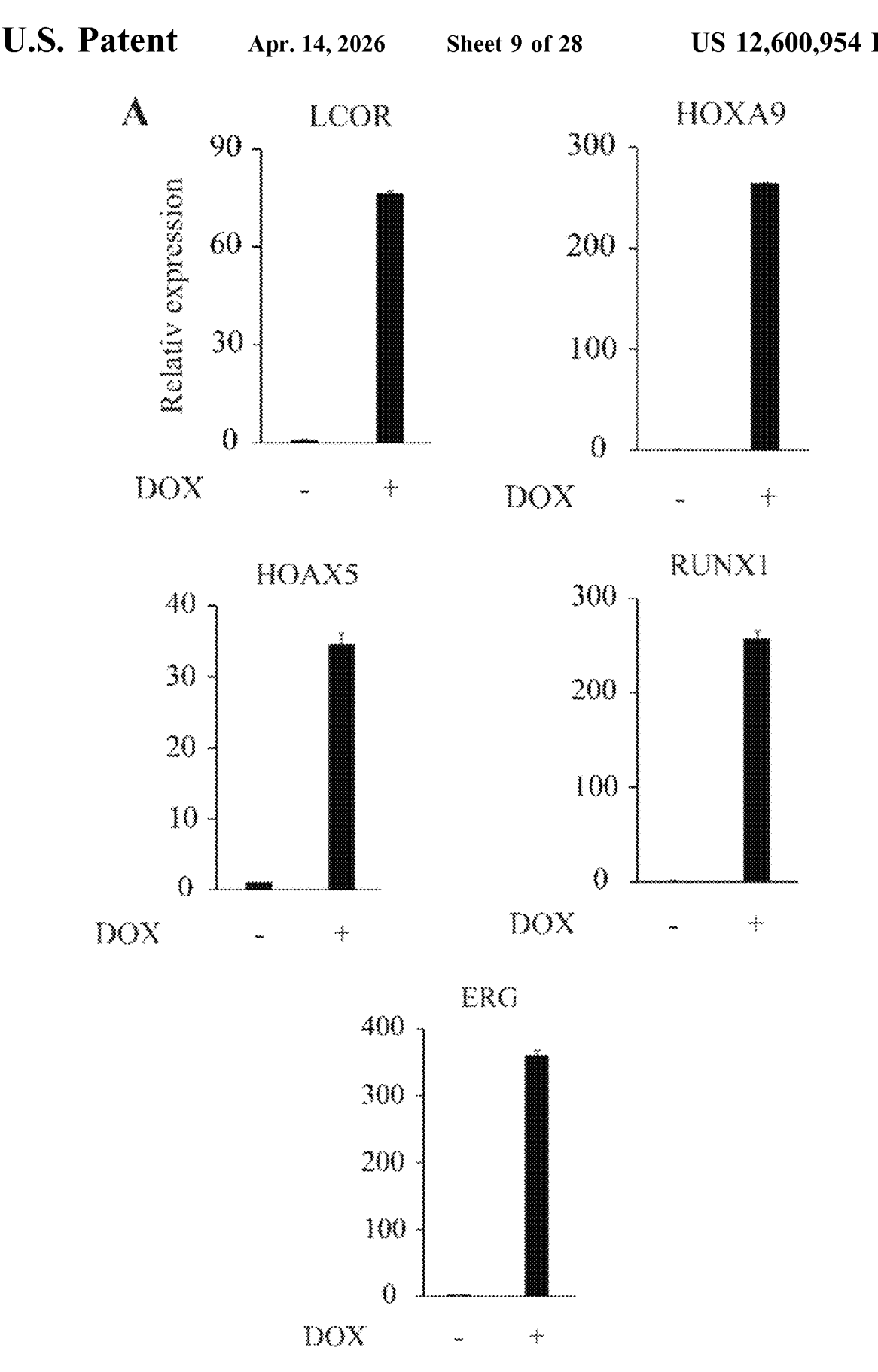
FIGS. 3A-3E illustrate overexpression of LHHRE to promote the generation of long-term repopulating hematopoietic stem cells according to some embodiments of the present disclosure.
Figure 3B:
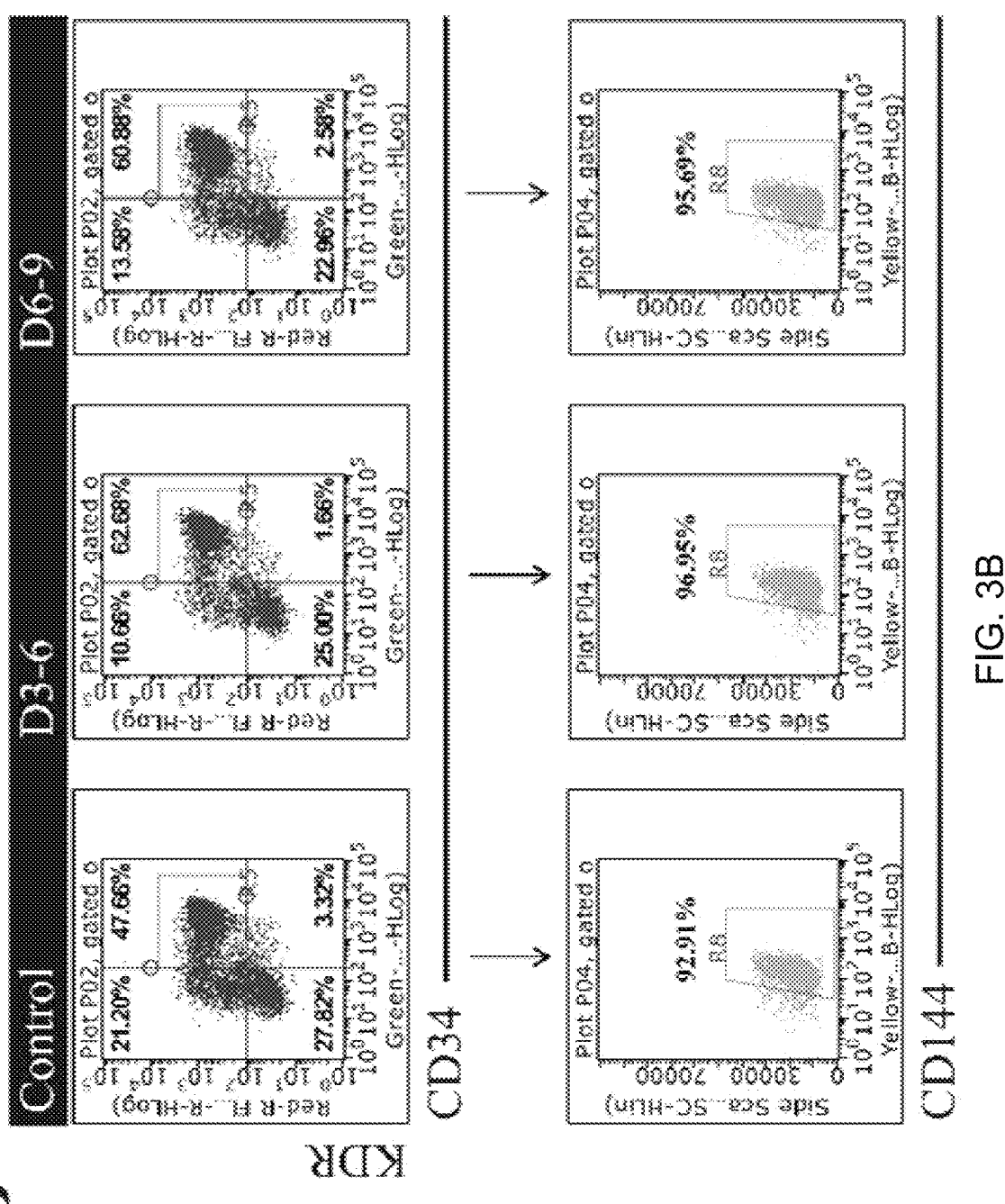
Figure 3C:
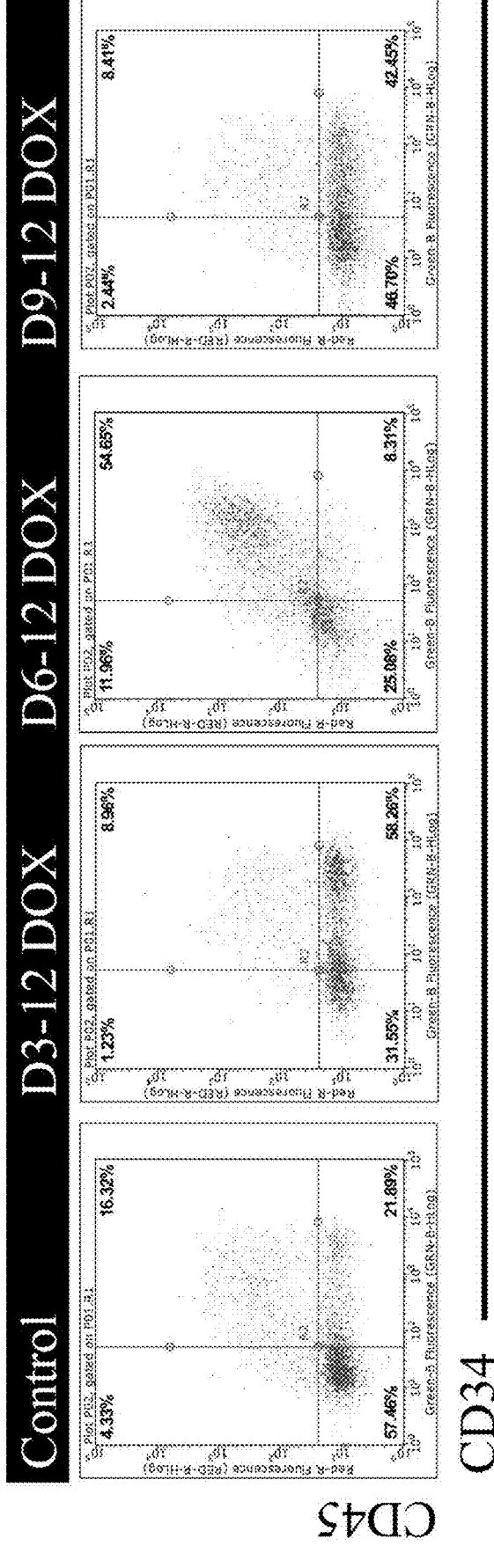

Embodiment 2 Effect of Inducing LHHRE at Different Times on the Production of the Hematopoietic Endothelial Cells and the Hematopoietic Stem Cells The stable transfected cell line hiPS-001-5-LHHRE obtained in Embodiment 1 was identified. As shown in FIG. 3A, it indicates that DOX can induce transcriptional expression of the inserted genes LCOR, HOXA9, HOXA5, RUNX1, and ERG. In order to investigate the effect of stage-specific expression of LCOR, HOXA9, HOXA5, RUNX1, and ERG on the differentiation of the hematopoietic stem cells, the present embodiment added DOX at different time windows of induced differentiation to induce the expression of the above genes. The flow cytometry analysis on day 9 of differentiation indicates that the induction efficiency of $CD34^+KDR^+CD144^+$ hematopoietic endothelial cells in the control group is 44.28% (Control, 47.66%×92.91%); whereas, the induction efficiency of the $CD34^+KDR^+CD144^+$ hematopoietic endothelial cells in the experimental groups supplemented with DOX on days 3-6 and 6-9 of differentiation significantly increases to 60.77% (D3-6 DOX, 62.68%×96.95%) and 58.26% (D6-9 DOX, 60.88%×95.69%), respectively. The results of the above experiments indicate that overexpression of LHHRE is beneficial to enhance generation of the hematopoietic endothelial cells, as shown in FIG. 3B. As shown in FIG. 3C, the flow cytometry analysis on day 12 of differentiation indicates that the addition of DOX on days 3-12, 6-12, and 9-12 all significantly increases the induction efficiency of $CD34^+$ cells; however, only the addition of DOX on days 6-12 significantly increases the induction of $CD34^+CD45^+$ cells, with an induction efficiency of 54.65%, and the induction efficiencies of $CD34^+CD45^+$ cells in the control group and the experimental groups with the addition of DOX on days 3-12 and 9-12 are 16.32%, 8.96%, and 8.41%, respectively.

Figure 3D:
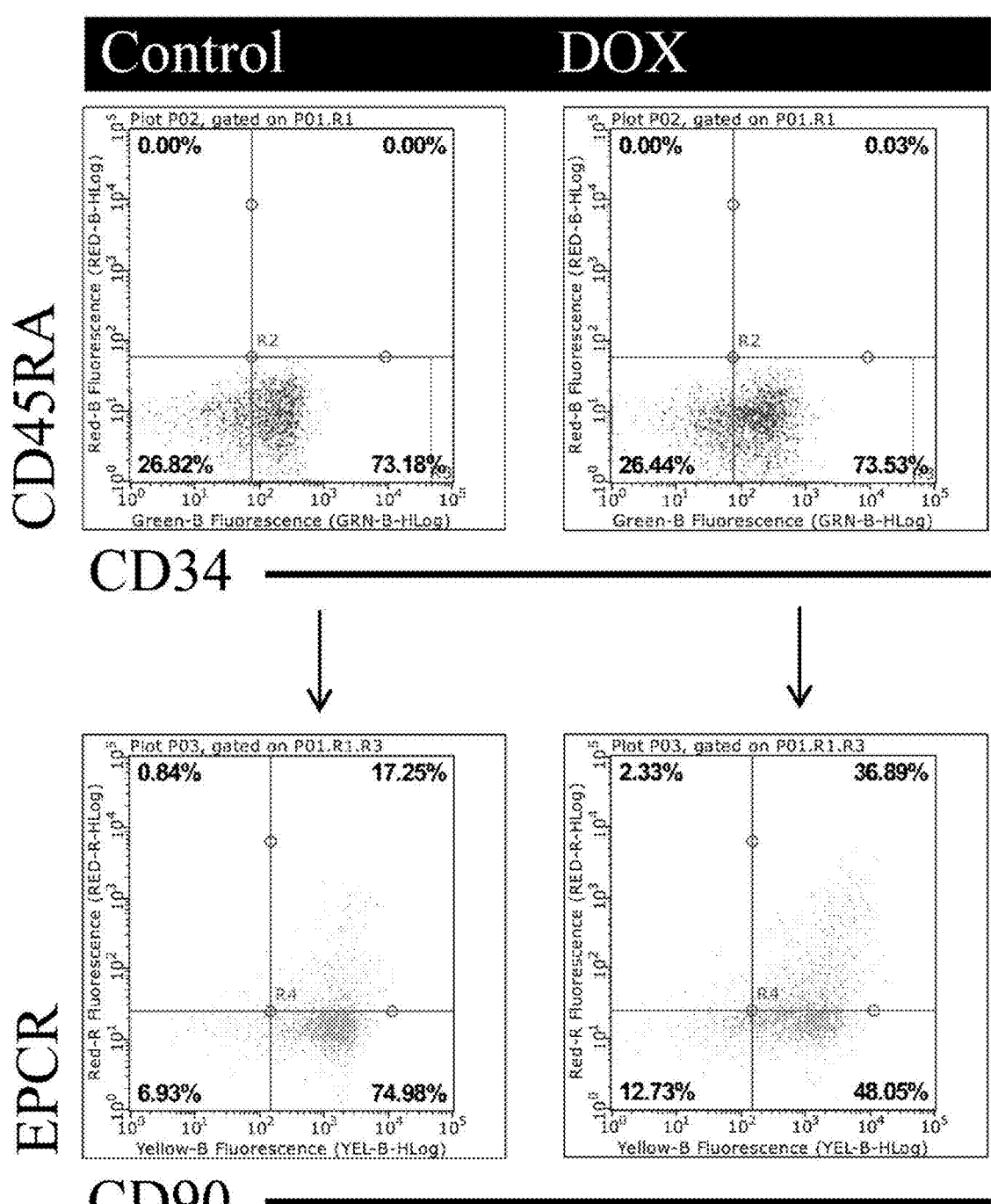
Figure 3E:
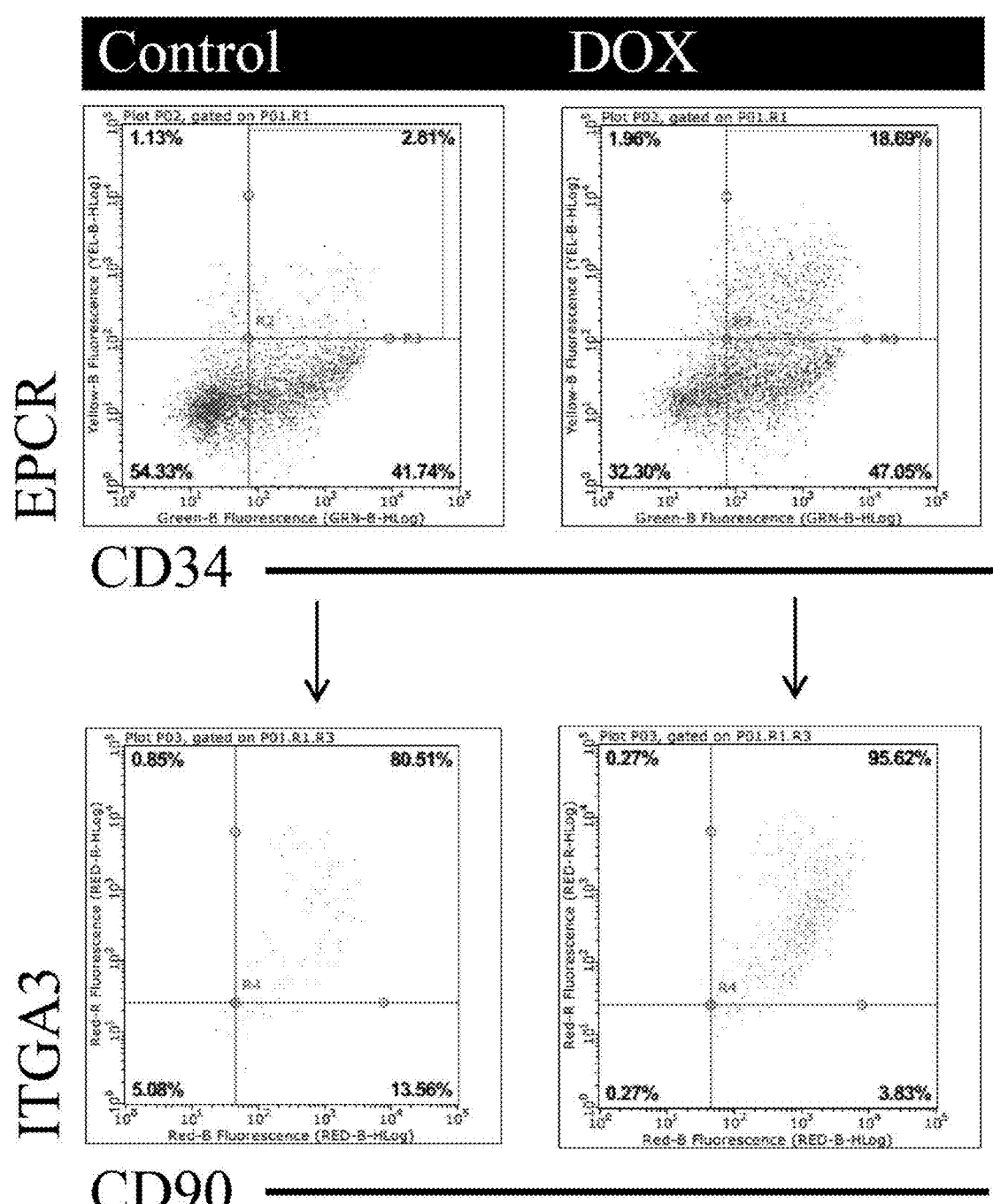

Based on the above experimental results, the treatment time of DOX is determined to be days 6-12 of differentiation. In order to investigate the effect of overexpression of LHHRE on the differentiation of the hematopoietic stem cells, this embodiment examined the expression of marker genes of the hematopoietic stem cells. As shown in FIGS. 3D-3E, the flow cytometry analysis on day 12 of differentiation indicates that the addition of DOX increases the induced differentiation efficiency of $CD34^+CD45RA^-CD90^+EPCR^+$ hematopoietic stem cells (DOX VS. Control, 27.13% VS. 12.62%) and $CD34^+EPCR^+CD90^+ITGA3^+$ long-term repopulating hematopoietic stem cells (DOX VS. Control, 17.87% VS. 2.26%).

The above experimental results indicate that overexpression of LHHRE not only enhances the induction of hematopoietic endothelial cells, but also promotes the generation of the long-term repopulating hematopoietic stem cells.

Figure 4:
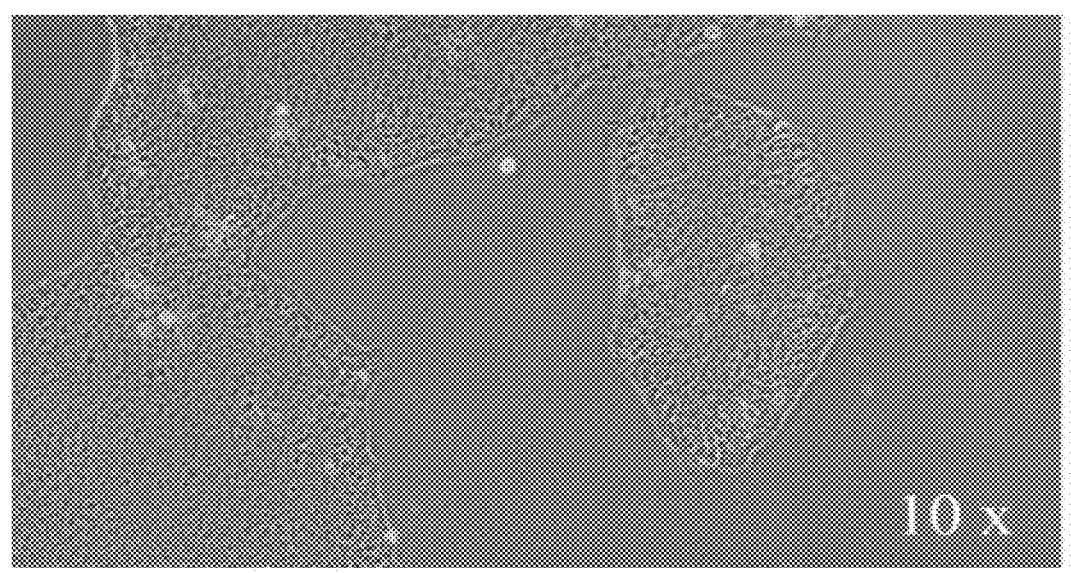
FIG. 4 is cell morphology images of human pluripotent stem cells (hiPS-001-5-LHHRE) before passage (Day–1) at different magnifications according to some embodiments of the present disclosure.
Figure 4:
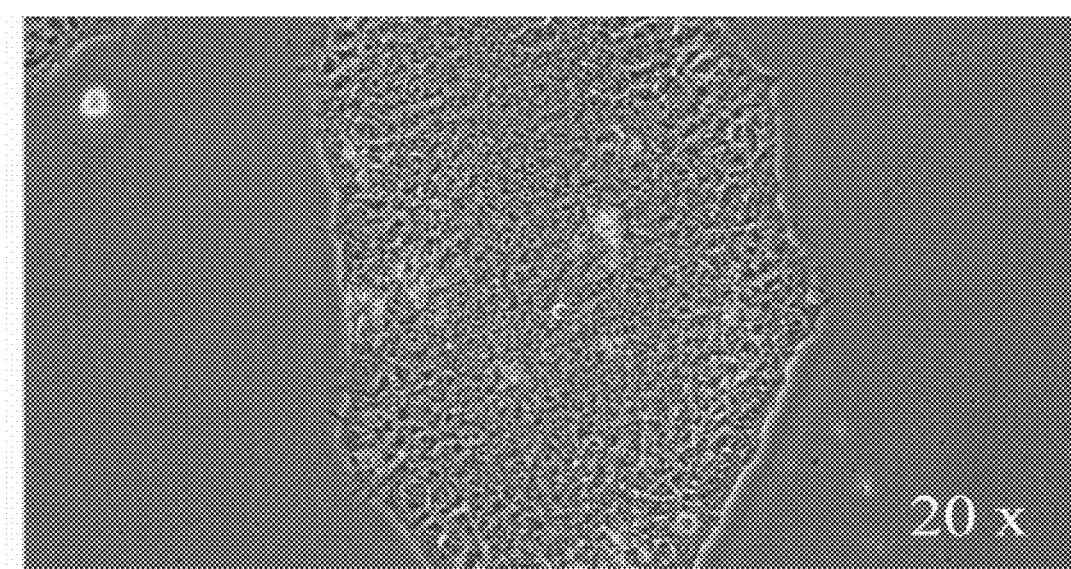

Embodiment 3 Differentiation Process of the Human Pluripotent Stem Cells Into the Hematopoietic Stem Cells 3.1 Formation of Monolayer Adherent Cells Experimental operation: Day−1
1) Taking an appropriate volume of TrypLE working solution and placing it in a 37° C. water bath to preheat for 10 min.
2) Preparing TeSR-E8 medium including 10 µM Y-27632 according to the amount of medium required for passaging by adding 1 µL of Y-27632 (10 mM) stock solution per 1 mL of TeSR-E8 medium. Preheating in the 37° C. water bath for 10 min.
3) Taking the hiPSC-001-5 cells to be passaged from the incubator (cell morphology as shown in FIG. 4, observed under a common light microscope observation, a cell confluence of human pluripotent stem cells (hiPS-001-5-LHHRE) before passaging was 70%-80%; the edge of the cell clone was smooth, no obvious differentiation of the cells, the cells were tightly arranged, and had a good three-dimensional structure), aspirating and discarding the original medium and washing it twice with DPBS (with the volume of DPBS not less than the volume of the original medium for each washing), for 1 min each time (when washing, leaving the DPBS in the well/bottle for 30-45 s before aspiration).
4) Adding TrypLE working solution (about 1 mL TrypLE working solution for the six-well plate, about 2 mL TrypLE working solution for the T25 bottle) to make it cover the bottom of the plate uniformly, and place the six-well plate or the T25 bottle in the incubator to incubate for 2-5 min; and observing under the microscope until the cells shrink, become round, and disperse.
5) Gently tapping the culture flask/plate to detach the cells from the bottom of the plate, then gently blowing several times with a pipette, and finally adding an equal volume of digestion termination solution to terminate the digestion.
6) Centrifuging the cells at 200 g for 5 min after balancing, aspirating and discarding the supernatant after centrifugation, flicking the bottom of the centrifuge tube to fully disperse the cells, and then resuspending the cells by adding an appropriate volume of TeSR-E8 medium including 10 µM Y-27632, and then adjusting to the appropriate cell density after cell counting.
7) Taking the Matrigel-coated plates/bottles, removing the remaining coating solution and washing once with DPBS. Inoculating the well-mixed cell suspension onto the coated culture plate/bottle at a density of 8000 cells/cm², labeled with information such as the date of passage, the cell type, and the number of cell generations. Placing the culture plates/bottles in 37° C., 5% $CO_2$ incubator for static incubation.

Note: controlling the cell inoculation density at 8,000-10,000 cells/cm$^2$, and not shaking the plate/bottle after inoculation to prevent cells from aggregating in the center of the plate/dish.

3.2 Mesoderm Induction

Experimental operation: Day 0

1) Taking an appropriate amount of the mesoderm induction medium and placing it in a 37° C. water bath to preheat for 10 min.

Figure 5:
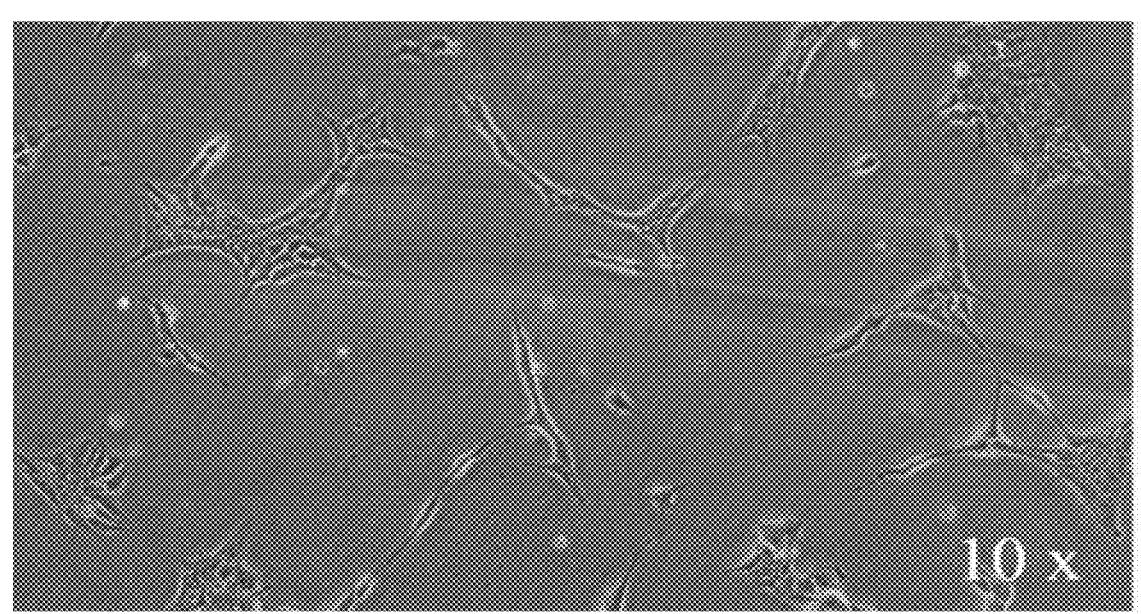
FIG. 5 is cell morphology images of the human pluripotent stem cells (hiPS-001-5-LHHRE) before induced differentiation (Day0) at the different magnifications according to some embodiments of the present disclosure.
Figure 5:
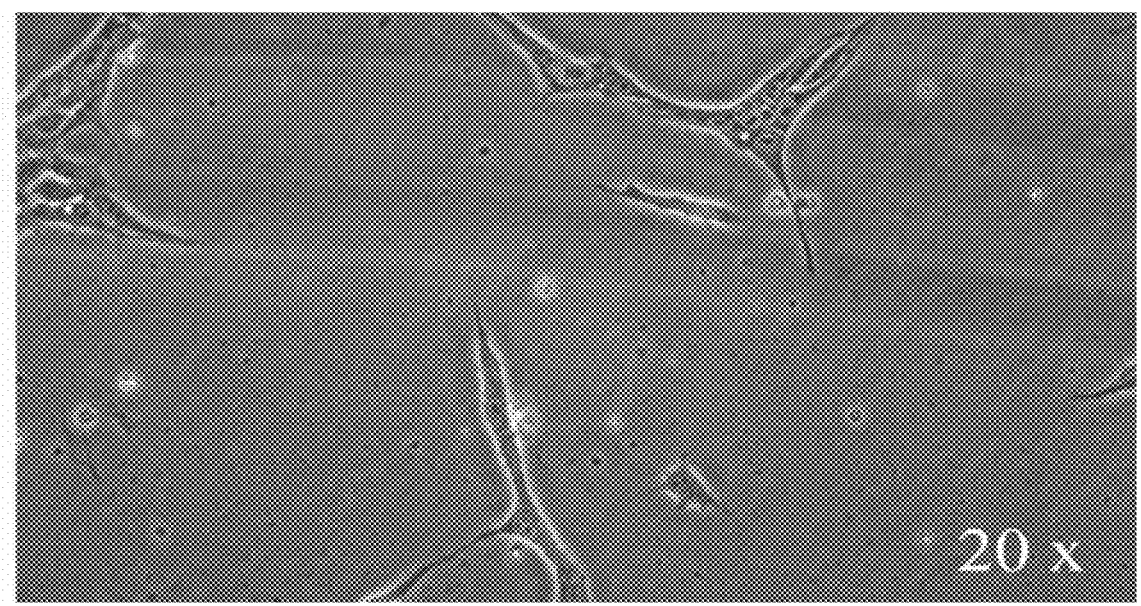

2) After 24 h of monolayer adherent cell formation, taking out the cells to be differentiated from the incubator (cell morphology as shown in FIG. 5, observed under a common light microscope, human pluripotent stem cells (hiPS-001-5-LHHRE) formed small clones before induced differentiation), aspirating and discarding the original culture medium, adding an appropriate volume of DPBS to wash the cells and washing twice with DPBS (the volume of DP BS not less than the volume of original culture medium for each washing) for 1 min each time (when washing, leaving the DBPS in the plate/bottle for 30-45 s before aspirating).

3) Adding the mesoderm induction medium, and then placing in a 37° C., 5% CO$_2$ incubator for static culture for 24 h (adding 2 mL of culture solution to each well of a 6-well culture plate).

3.3 Hematopoietic Mesoderm Differentiation

Experimental operation: Day1.

1) Taking the appropriate amount of a hematopoietic mesoderm differentiation medium and placing it in a 37° C. water bath to preheat for 10 min.

Figure 7:
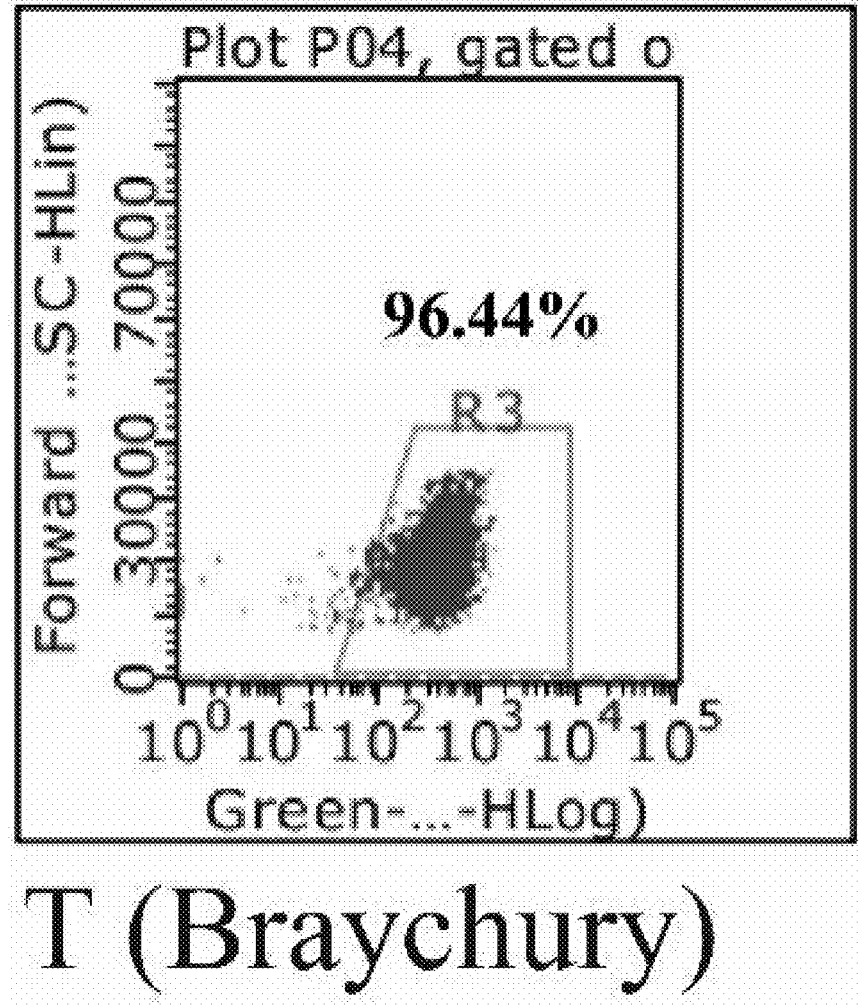
FIG. 7 is a result of flow cytometry analysis of mesodermal markers during the induction of differentiation of the human pluripotent stem cells (hiPS-001-5-LHHRE) (Day1) according to some embodiments of the present disclosure.

2) After 24 h of mesoderm induction, taking the differentiated cells from the incubator (cell morphology as shown in FIG. 6, observed under a common light microscope, human pluripotent stem cells (hiPS-001-5-LHHRE) cells induced to differentiate into the mesodermal cells, and the edge of the cell clone obviously shrunk after the mesoderm induction; the flow cytometry detection results of mesodermal markers were shown in FIG. 7, and the expression of the mesodermal cell marker T (Braychury) in the induced differentiation of human pluripotent stem cells (hiPS-001-5-LHHRE) was analyzed through cell flow cytometry, specific detection methods were detailed in the cell flow cytometry of the experimental methods section, after the mesoderm induction, edges of cell clones should shrink, and the induction efficiency of the mesoderm marker T (Braychury) detected by flow cytometry should reach more than 90%), aspirating and discarding the original culture medium, adding an appropriate volume of DPBS to wash the cells, and washing the cells twice with DPBS (with the volume of DPBS not less than that of the original culture medium for each washing) for 1 min each time (when washing, leaving the DPBS in the plate/flask for 30-45 s before aspirating).

3) Adding the hematopoietic mesoderm differentiation medium, and then placing in a 37° C., 5% CO$_2$ incubator for static culture for 48 h (adding 2 mL of culture medium to each well of a 6-well culture plate).

3.4 Hemogenic Endothelium Differentiation and Endothelial-to-Hematopoietic Transition (ETH)

Experimental operation: Day3.

1) Taking the appropriate amount of prepared hematopoietic endothelial differentiation and endothelial-hematopoietic cell transformation medium and place it in a 37° C. water bath to preheat for 10 min.

2) Taking an appropriate volume of TrypLE working solution and place it in a 37° C. water bath to preheat for 10 min.

Figure 9:
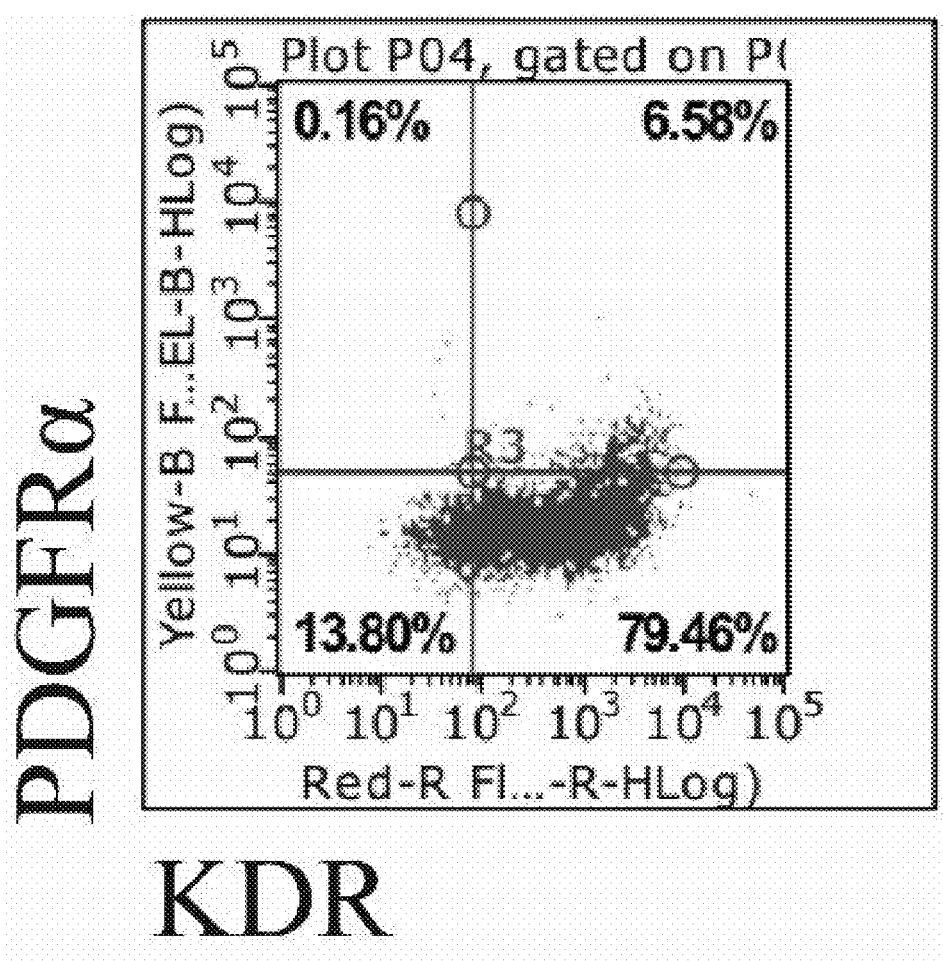
FIG. 9 is a result of a flow cytometry analysis of the hematopoietic mesodermal markers during the induction of differentiation of the human pluripotent stem cells (hiPS-001-5-LHHRE) (Day3) according to some embodiments of the present disclosure.

3) After 48 h of the hematopoietic mesoderm differentiation, taking the differentiated cells from the incubator (cell morphology as shown in FIG. 8, observed under a common light microscope, human pluripotent stem cells (hiPS-001-5-LHHRE) induced to differentiate into the hematopoietic mesodermal cells, the cells proliferated rapidly after the induction, and the cells showed mesenchymal-like morphology, with a polygonal shape and relatively loose arrangement; the flow cytometry detection results of mesodermal marker were shown in FIG. 9, the expression of hematopoietic mesodermal cell markers KDR and PDGFRα in the induced differentiation of human pluripotent stem cells (hiPS-001-5-LHHRE) was analyzed by cell flow cytometry, and the specific detection method was described in detail in the cell flow cytometry of the experimental methods section, during the hematopoietic mesoderm induction phase, the cells undergo rapidly proliferation and spread, compared with the compact clones, the cells become relatively loose, the proportion of hematopoietic mesoderm cells KDR$^+$ PDGFRα$^-$ detected by the flow cytometry should be above 70%, and an inoculation density of cell passage was controlled at $1 \times 10^4$ cells/cm$^2$-$4 \times 10^4$ cells/cm$^2$), aspirating and discarding the original culture medium, adding an appropriate volume of DPBS to wash the cells, and washing the cells twice with DPBS (with the volume of DPBS not less than the amount of the original culture medium for each washing) for 1 min each time (when washing, leaving the DBPS in the plate/bottle for 30-45 s before aspirating).

4) Adding TrypLE working solution (1 mL TrypLE working solution per well of a 6-well culture plate) to make it cover the bottom of the plate uniformly, and placing in the incubator for incubation for 2-5 min, and observing under the microscope until the cells shrink and become round, and disperse.

5) Gently tapping the culture flask/plate to detach the cells from the bottom of the plate, then gently blowing several times with a pipette, and finally adding an equal volume of a terminal digestion solution to terminate the digestion.

6) Centrifuging at 200 g for 5 min after balancing, aspirating and discarding the supernatant after centrifugation, flicking the bottom of the centrifuge tube to make the cells well dispersed, and then resuspending the cells by adding an appropriate amount of the hematopoietic endothelial differentiation and endothelial-hematopoietic cell transformation medium including 10 μM Y-27632, and then adjusting to an appropriate cell density after cell counting.

7) Taking the Matrigel-coated culture plate/bottle, removing the remaining coating solution and washing once with DPBS. Inoculating the well-mixed cell suspension into the coated culture plates/flasks at an inoculation density of $2 \times 10^4$ cells/cm$^2$, labeled with information such as the date of passage, cell type, and the number of cell generations, and then placing in a 37° C., 5% CO$_2$ incubator for static incubation (adding 2 mL of culture solution to each well of a 6-well culture plate).

Experimental operation: Day4

1) Taking the appropriate amount of prepared hematopoietic endothelial differentiation and endothelial-hematopoietic cell transformation medium and placing it in a 37° C. water bath to preheat for 10 min.

2) Taking the differentiated cells from the incubator (cell morphology as shown in FIG. 10, observed under a common light microscope, the human pluripotent stem cells (hiPS-001-5-LHHRE) induced to differentiation into the hematopoietic endothelial cells, after re-passage, the cell density was low, and the cells were still mesenchymal-like cell morphology, with a polygonal shape), aspirating and discarding the original culture medium, and replacing with fresh hematopoietic endothelial differentiation and endothelial-hematopoietic cell transformation medium, and then placing in a 37° C., 5% $CO_2$ incubator for static culture (adding 2 mL of culture medium to each well of a 6-well culture plate).

Experimental operation: Day6.

1) Taking the appropriate amount of hematopoietic endothelial differentiation and endothelial-hematopoietic cell transformation medium including 5 μg/mL DOX, and place in a 37° C. water bath to preheat for 10 min.

Figure 12:
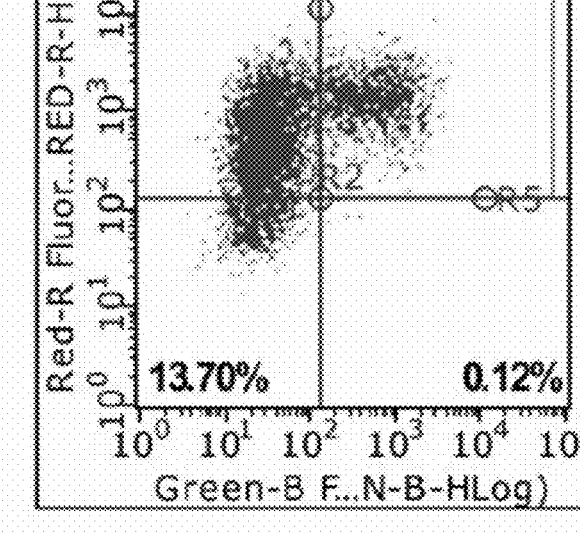
FIG. 12 is results of flow cytometry analysis of the hematopoietic endothelial cells markers during the induction of differentiation of the human pluripotent stem cells (hiPS-001-5-LHHRE) (Day6) at the different magnifications according to some embodiments of the present disclosure.
Figure 12:
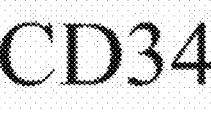
Figure 12:
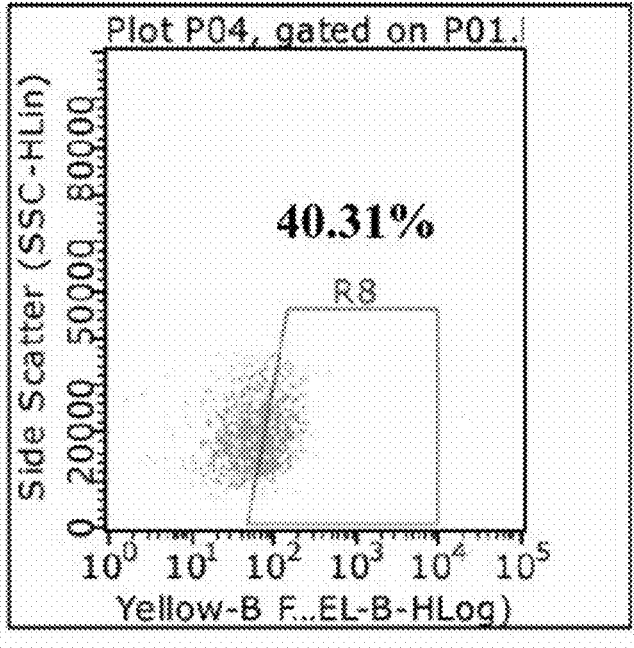

2) Taking the differentiated cells from the incubator (cell morphology as shown in FIG. 11, observed under a common light microscope, the human pluripotent stem cells (hiPS-001-5-LHHRE) induced to differentiation into the hematopoietic endothelial cells, the cells proliferated rapidly to generate a larger number of the hematopoietic endothelial cells, the cells are arranged tightly, in a spindle shape, with a clear nucleolus; the flow cytometry detection results of the hematopoietic endothelial cell markers CD34, KDR and CD144 were shown in FIG. 12, the expression of hematopoietic endothelial cells markers CD34, KDR, and CD144 in induced differentiation of human pluripotent stem cells (hiPS-001-5-LHHRE) was analyzed by the cell flow cytometry, the specific detection method was described in detail in the cell flow cytometry of the experimental methods section, during the hematopoietic endothelial phase, the cells gradually changed from the mesenchymal-like cells into hematopoietic endothelial-like cells, in a spindle shape, with a tightly arrangement and an obvious nucleoli, the hematopoietic endothelial cell markers CD34, KDR, and CD144 were detected by the flow cytometry, and the proportion of $CD34^+KDR^+$ cells should be no less than 20%, and the proportion of $CD144^+$ cells in $CD34^+KDR^+$ cells should be no less than 30%), aspirating and discarding the original culture medium, and replacing it with the fresh hematopoietic endothelial specialization and endothelial-to-hematopoietic transition medium including 5 μg/mL of DOX, and then placing in 37° C., 5% $CO_2$ incubator for static culture (adding 2 mL of culture medium to each well of the 6-well culture plate).

Experimental operation: Day8

1) Taking the appropriate amount of hematopoietic endothelial differentiation and endothelial-hematopoietic cell transformation medium including 5 μg/mL DOX, and place it in a 37° C. water bath to preheat for 10 min.

2) Taking the differentiated cells from the incubator, aspirating and discarding the original culture medium, replace it with fresh hematopoietic endothelial differentiation and endothelial-hematopoietic cell transformation medium including 5 μg/mL DOX, and then place it in a 37° C., 5% $CO_2$ incubator for static culture (adding 2 mL of culture medium to each well of the 6-well culture plate).

Figure 13:
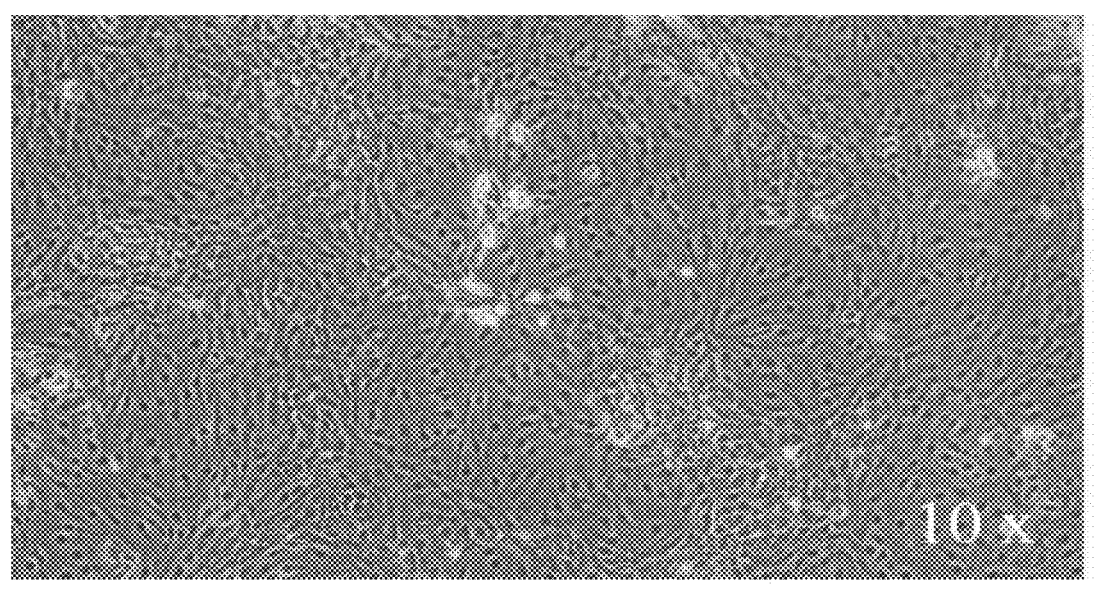
FIG. 13 is cell morphology images of the human pluripotent stem cells (hiPS-001-5-LHHRE) induced to differentiate into hematopoietic stem and progenitor cells (Day9) at the different magnifications according to some embodiments of the present disclosure.
Figure 13:
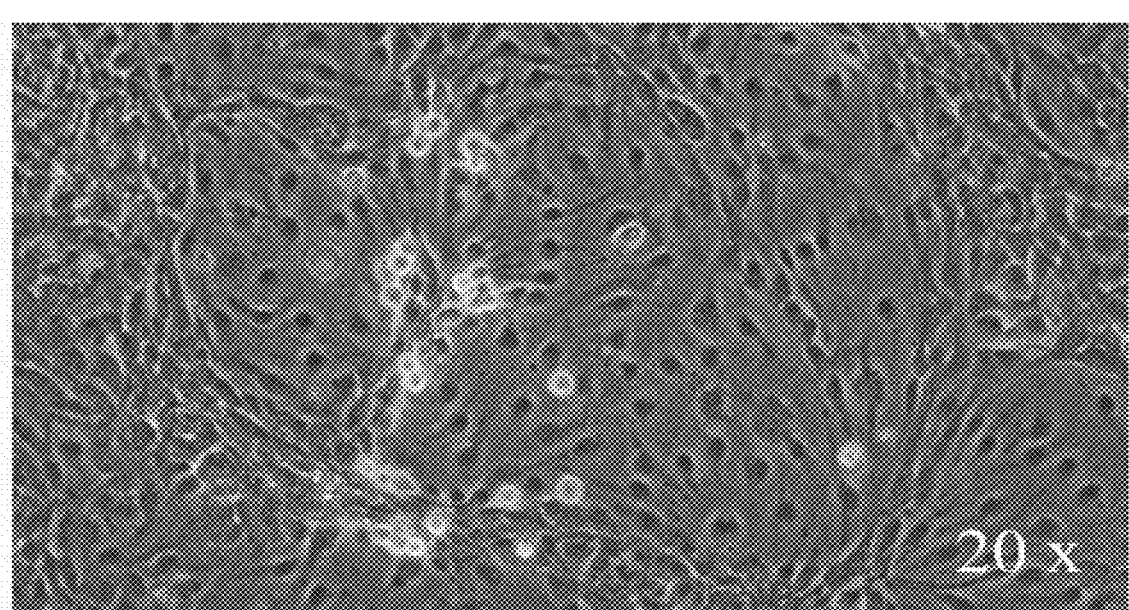
Figure 14:
FIG. 14 is results of flow cytometry analysis of the hematopoietic endothelial cells markers during the induction of differentiation of the human pluripotent stem cells (hiPS-001-5-LHHRE) (Day9) at the different magnifications according to some embodiments of the present disclosure.
Figure 14:
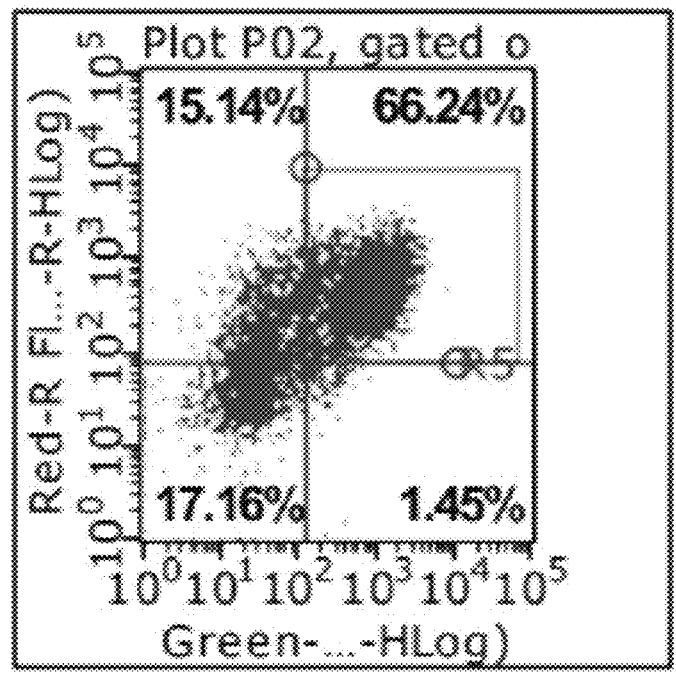
Figure 14:
Figure 14:
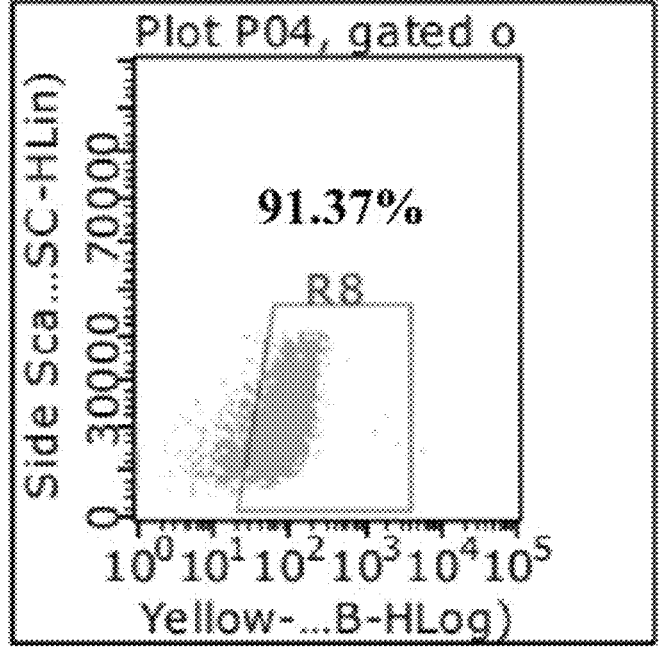

3) Observing the cell morphology on Day9 and detecting the expression of the hematopoietic endothelial cell markers CD34, KDR, and CD144 by the flow cytometry, as detailed in the cell flow cytometry of the experimental methods section. The results were shown in FIG. 13 and FIG. 14, respectively. As observed by the common light microscopy, human pluripotent stem cells (hiPS-001-5-LHHRE) induced to differentiate into the hematopoietic stem and progenitor cells, the hematopoietic endothelial cells migrated and aggregated to form hematopoietic centers, and a small number of non-adherent and round hematopoietic stem and progenitor cells began to appear. Through the cell flow cytometry, the expression of the hematopoietic endothelial cell markers CD34, KDR, and CD144 in the induced differentiation of the human pluripotent stem cells (HS-001-5-LHHRE) was detected. During the hematopoietic endothelial phase, the hematopoietic endothelial cells migrated to form hematopoietic centers and a small number of suspended cells appeared. The hematopoietic endothelial cell markers CD34, KDR, and CD144 were detected by the flow cytometry, and the proportion of $CD34^+KDR^+$ cells should be no less than 50%, and the proportion of $CD144^+$ cells in $CD34^+KDR^+$ cells should be no less than 80%.

Experimental operation: Day10

1) Taking the appropriate amount of hematopoietic endothelial differentiation and endothelial-hematopoietic cell transformation medium including 5 μg/mL DOX, and place it in a 37° C. water bath to preheat for 10 min.

2) Taking the differentiated cells from the incubator, collecting the original culture medium into a 15 mL centrifuge tube, centrifuging at 200 g for 5 min after balancing, aspirating and discarding the supernatant after centrifugation, flicking the bottom of the centrifuge tube to make the cells well dispersed, and then resuspending the cells by adding an appropriate amount of hematopoietic endothelial differentiation and endothelial-hematopoietic cell transformation medium including 5 μg/mL DOX.

3) Re-inoculating resuspended cells into culture plates/flasks, and then placing in a 37° C., 5% $CO_2$ incubator for static incubation (adding 2 mL of culture solution to each well of the 6-well culture plate).

Experimental Operation: Day12

Figure 15:
FIG. 15 is cell morphology images of the human pluripotent stem cells (hiPS-001-5-LHHRE) induced to differentiated into hematopoietic stem cells (Day12) at the different magnifications according to some embodiments of the present disclosure.
Figure 15:
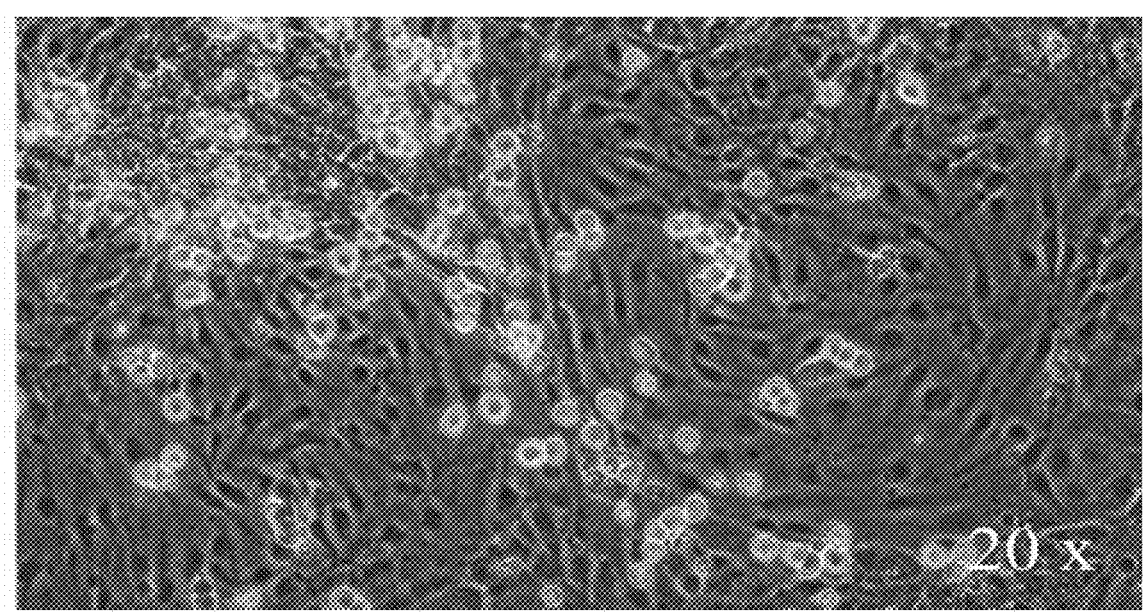
Figure 16:
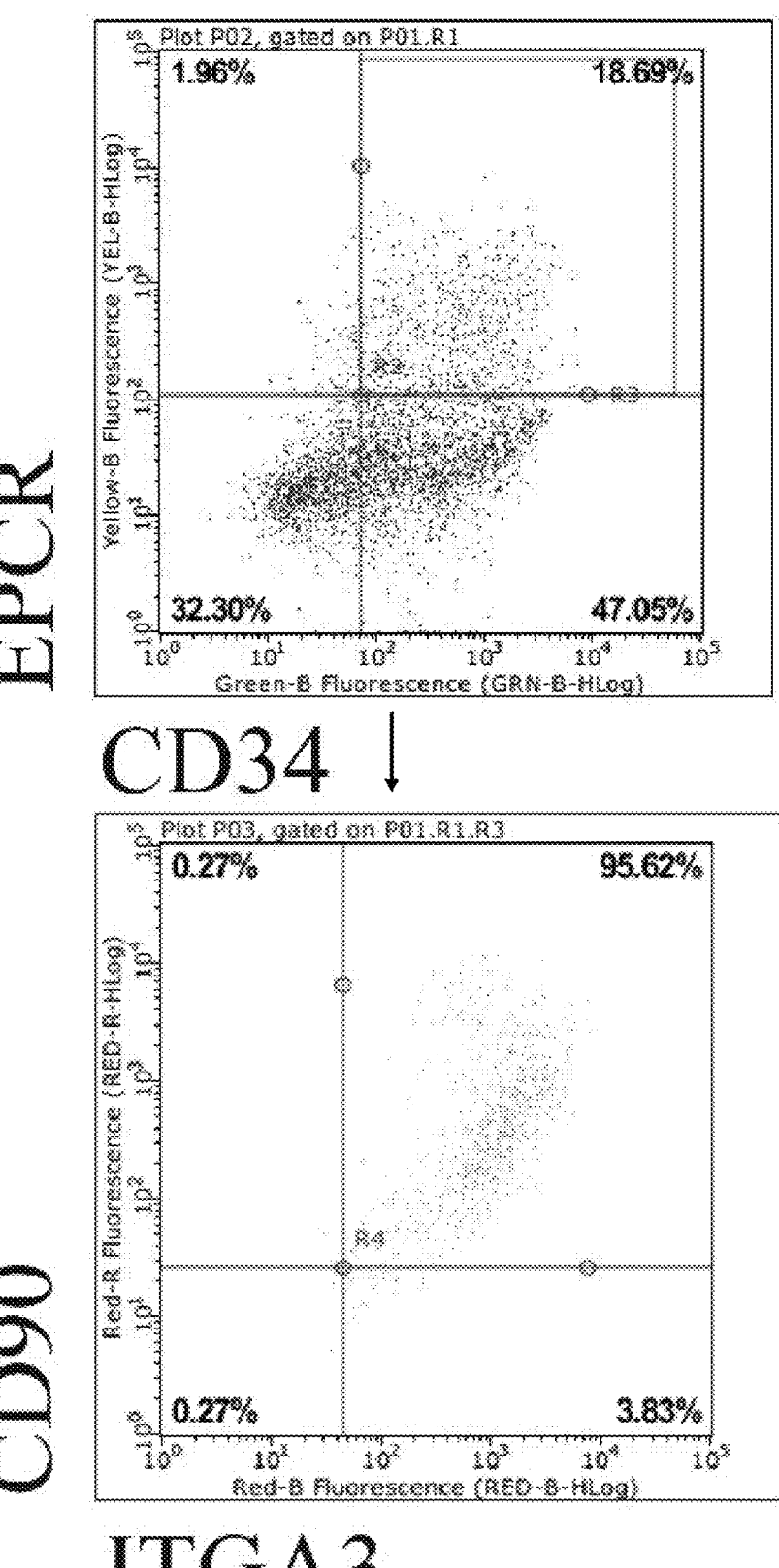
FIG. 16 is results of flow cytometry analysis of the hematopoietic stem cells markers during the induction of differentiation of the human pluripotent stem cells (hiPS-001-5-LHHRE) (Day12) according to some embodiments of the present disclosure.

Taking the differentiated cells from the incubator (cell morphology and the flow cytometry results for the long-term repopulating hematopoietic stem cells markers CD34, CD90, EPCR, and ITGA3 were shown in FIG. 15 and FIG. 16, respectively, the human pluripotent stem cells (hiPS-001-5-LHHRE) were induced to differentiate into the hematopoietic stem cells and formed a large number of non-adherent and round hematopoietic stem and progenitor cells. By cell flow cytometry, the expression of the long-term repopulating hematopoietic stem cell markers CD34, CD90, EPCR, and ITGA3 in the induced differentiation of the human pluripotent stem cells (hiPS-001-5-LHHRE) was detected, the specific detection method was described in detail in the cell flow cytometry of the experimental methods section, the pipette could be used to repeatedly rinse the cells during the detection, to ensure that most of the non-adherent round cells were collected), collecting the original culture medium into a 15 mL centrifuge tube, centrifuging at 200 g for 5 min after balancing, aspirating and discarding the supernatant after centrifugation, and flicking the bottom of the centrifuge tube to make the cells fully dispersed, and then using the obtained hematopoietic stem cells for the subsequent experiments or freeze storage.

Figure 17A:
FIGS. 17A-17B illustrate verification of in vitro differentiation potential of the hematopoietic stem cells by colony-forming unit assays (CFU) according to some embodiments of the present disclosure.
Figure 17A:
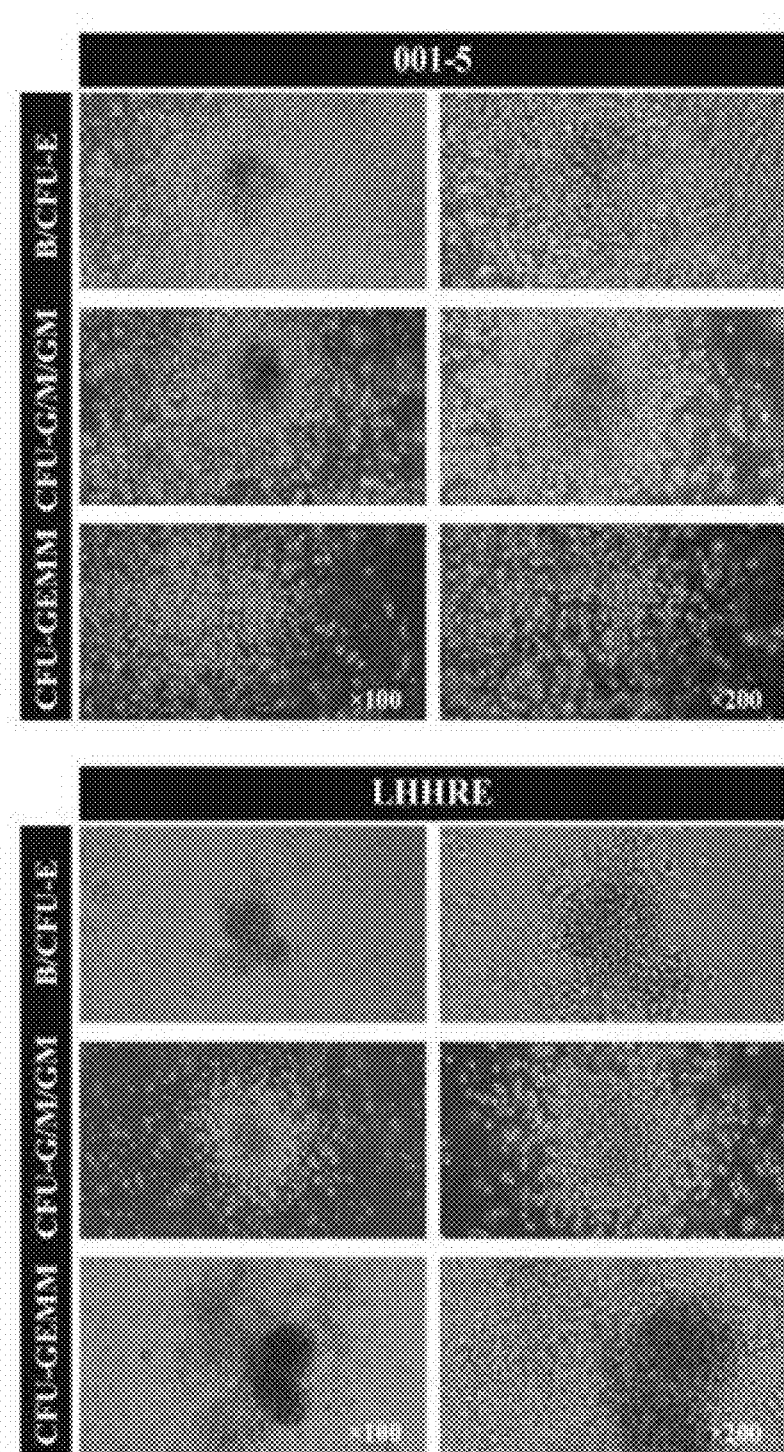
Figure 17B:
Figure 17B:
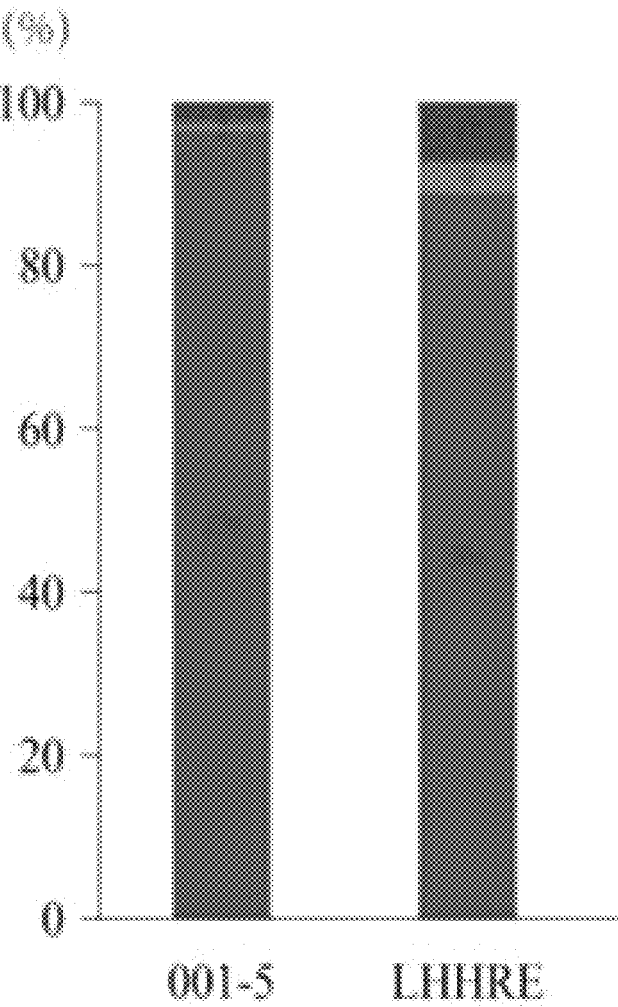

Embodiment 4 Validation of Differentiation Potential of the Hematopoietic Stem Cells Hematopoietic stem cells are cells with self-renewal and differentiation potential, which can differentiate into all blood cells (Giebel and Bruns, 2008; Seita and Weissman, 2010). In order to assess the in vitro differentiation potential of the hematopoietic stem cells obtained by induced differentiation according to some embodiments of the present disclosure, a colony forming unit assay (CFU) was performed. Suspension cells obtained by hiPS-001-5 and hiPS-001-5-LHHRE induced differentiation (prepared in Embodiment 3) were cultured in the methylcellulose medium for 14 days to all form erythrocyte (BFU-E and CFU-E), granulocyte (CFU-G), macrophage (CFU-M), granulocyte/macrophage (CFU-GM), and multilineage progenitor cell (CFU-GEMM) colony units, as shown in FIG. 17A. The above experiments demonstrate that the suspension cells obtained by induced differentiation all contain hematopoietic stem and progenitor cells with the potential to differentiate into multilineage blood cells. As shown in FIG. 17B, the total number of colonies formed by the suspension cells obtained by hiPS-001-5 and hiPS-001-5-LHHRE induced differentiation was similar (001-5 Vs. LHHRE: 237 VS. 232), but relative to hiPS-001-5, an efficiency of forming the erythrocyte colonies from suspension cells obtained by hiPS-001-5-LHHRE induced differentiation is significantly improved (001-5 VS. LHHRE: 3.38% VS. 11.21%).

The above experiments indicate that hematopoietic stem and progenitor cells obtained by in vitro induced differentiation according to some embodiments of the present disclosure possess a multilineage hematopoietic cell differentiation potential, and the hematopoietic stem and progenitor cells obtained by overexpression of LHHRE have a higher erythroid lineage differentiation potential, and are closer to the hematopoietic stem cells from umbilical cord blood in terms of differentiation potential.

Currently, targeted differentiation of the hematopoietic stem cells from the human pluripotent stem cells is achieved by simulating the process of the development of the hematopoietic stem cells in vivo and stage-specifically regulating the key signaling pathways related to the development of the hematopoietic stem cells, thereby achieving in vitro induced differentiation of the hematopoietic stem cells. However, most of the cells obtained by this method are hematopoietic progenitor cells, and the content of the hematopoietic stem cells is extremely low. The development of the hematopoietic stem cells is regulated by a cascade of key transcription factors. Cellular transcription factors determine cell fate by regulating gene expression, and overexpression of key transcription factors enables reprogramming of the cell fate. It has been indicated that constitutive expression of the transcription factors FOSB, GFI1, RUNX1, and SPI1 (FGRS) in combination with vascular cell co-culture can transform human adult endothelial cells into transplantable pluripotent hematopoietic progenitor cells (Lis et al., 2017; Sandler et al., 2014). Another study indicated that the transcription factors LCOR, HOXA5, HOXA9, RUNX1, and ERG (LHHRE) can reprogram the hematopoietic endothelial cells into hematopoietic stem/progenitor cells (Sugimura et al., 2017).

In order to improve the differentiation efficiency of LT-HSCs in vitro, the embodiments of the present disclosure constructs the LHHRE cell line to investigate the effects of the stage-specific overexpression of core transcription factors related to the regulation of hematopoietic stem cells development and the regulation of key signaling pathways related to the development of hematopoietic stem cells on the differentiation human pluripotent stem cells into hematopoietic stem cells. It is found that LHHRE promotes the generation of the long-term repopulating hematopoietic stem cells.

Embodiments of the present disclosure establish a serum-free differentiation system and an easy-to-operate differentiation process. By stage-specifically regulating key signaling pathways associated with the development of the hematopoietic stem cells and stage-specifically inducing the overexpression of the core transcription factors LCOR, HOXA9, HOXA5, RUNX1 and ERG associated with the developmental process of the hematopoietic stem cells through the Tet-on tetracycline-inducible expression system, it can achieve efficient differentiation from human pluripotent stem cells into $CD34^+EPCR^+CD90^+ITGA3^+$ long-term repopulating hematopoietic stem cells in vitro. The cells exhibit the differentiation potential into different hematopoietic cell colonies. In addition, it is found that LCOR, HOXA9, HOXA5, RUNX1 and ERG can promote the generation of $CD34^+KDR^+CD144^+$ hematopoietic endothelial cells.

Embodiments of the present disclosure provide a method for preparing the hematopoietic stem cells, in particular, to a method for preparing the hematopoietic stem cells by overexpressing LCOR, HOXA9, HOXA5, RUNX1, and ERG. The method brings following benefits: (1) adding the DOX to activate the expression of LHHRE in the stable cell cell line hiPS-001-5-LHHRE on days 6-12 of induced differentiation can achieve good differentiation effect of the hematopoietic stem cells; (2) overexpression of LHHRE can also promote the generation of $CD34^+KDR^+CD144^+$ hematopoietic endothelial cells. The existing literatures start with the hematopoietic endothelial cells and do not cover the effect of overexpression of LHHRE on the production of the hematopoietic endothelial cells. However, according to the embodiments of the present disclosure, DOX is added to initiate LHHRE overexpression on days 3-6 and days 6-9 (a generation phase of the hematopoietic endothelial cells) of differentiation. As a result, the induction efficiency of $CD34^+KDR^+CD144^+$ hematopoietic endothelial cells increases to 60.77% and 58.26%, respectively, whereas the induction efficiency of $CD34^+KDR^+CD144^+$ hematopoietic endothelial cells in control group (the addition of no DOX, no expression of LHHRE) is 44.28%; (3) the embodiments of the present disclosure not only improve the differentiation efficiency of hematopoietic stem cells and/or hematopoietic stem and progenitor cells, but also promote the generation of long-term repopulating hematopoietic stem cells.

What is claimed is:

1. A method for preparing hematopoietic endothelial cells, comprising:

(a) providing hematopoietic mesodermal cells comprising exogenously introduced nucleic acid sequences encoding transcription factors LCOR, HOXA9, HOXA5, RUNX1, ERG and an exogenously introduced nucleic acid sequence encoding reverse tetracycline transcriptional activator (rtTA) or a cell culture comprising the sequence modified hematopoietic mesodermal cells; wherein the nucleic acid sequences encoding the transcription factors LCOR, HOXA9, HOXAS, RUNX1, ERG and the nucleic acid sequence encoding rtTA are integrated in the genome of the hematopoietic mesodermal cells: the nucleic acid sequences encoding the transcription factors LCOR, HOXA9, HOXAS, RUNX1, ERG and the nucleic acid sequence encoding rtTA are operably linked to an inducible promoter, wherein the inducible promoter is a tetracycline-inducible promoter: the exogenous introduction of the nucleic acid sequences is carried out by a lentiviral vector:

(b) culturing the hematopoietic mesodermal cells or a cell culture comprising the sequence modified hematopoietic mesodermal cells in a hematopoietic endothelial differentiation medium; and (c) inducing the hematopoietic mesodermal cells to express the transcription factors LCOR, HOXA9, HOXAS, RUNX1, and ERG by adding tetracycline or doxycycline to the hematopoietic endothelial differentiation medium; wherein step (c) is performed on days 1-4 or days 4-7 of the culturing in step (b).

2. The method of claim 1, wherein in the step (c), the hematopoietic mesodermal cells overexpress the transcription factors LCOR, HOXA9, HOXA5, RUNX1, and ERG.

3. The method of claim 1, wherein the hematopoietic endothelial differentiation medium comprises VEGF, bFGF, SCF, IL-3, TPO, Flt-3L, and BMP4.

4. The method of claim 1, wherein the hematopoietic mesodermal cells or a cell culture comprising the sequence modified hematopoietic mesodermal cells are obtained by culturing mesodermal cells in a hematopoietic mesoderm differentiation medium.

5. The method of claim 4, wherein the hematopoietic mesodermal cells or a cell culture comprising the sequence modified hematopoietic mesodermal cells are obtained by culturing the mesodermal cells in the hematopoietic mesoderm differentiation medium for 2 days.

6. The method of claim 4, wherein the hematopoietic mesoderm differentiation medium comprises VEGF and bFGF.

7. The method of claim 4, wherein the mesodermal cells or the cell culture comprising the mesodermal cells are obtained by performing a mesoderm induction on pluripotent stem cells, wherein the pluripotent stem cells are induced pluripotent stem cells, wherein the induced pluripotent stem cells are human induced pluripotent stem cells.

8. The method of claim 7, wherein the pluripotent stem cells comprise the exogenously introduced nucleic acid sequences encoding the transcription factors LCOR, HOXA9, HOXA5, RUNX1, and ERG.

9. The method of claim 4, wherein the mesodermal cells are Braychury$^+$.

10. The method of claim 1, wherein the hematopoietic endothelial cells are CD34$^+$, KDR$^+$, and CD144$^+$.

11. The method of claim 1, wherein the hematopoietic mesodermal cells are KDR$^+$ and PDGFRα$^-$.

* * * * *